US009687605B2

(12) United States Patent
Yagi et al.

(10) Patent No.: US 9,687,605 B2
(45) Date of Patent: Jun. 27, 2017

(54) EXTRAVASATION DETECTING APPARATUS AND INFUSION SYSTEM

(75) Inventors: Akihiko Yagi, Kanagawa (JP); Takahiro Souma, Kanagawa (JP)

(73) Assignee: TERUMO KABUSHIKI KAISHA, Ashigarakami-Gun, Kanagawa (JP)

( * ) Notice: Subject to any disclaimer, the term of this patent is extended or adjusted under 35 U.S.C. 154(b) by 1093 days.

(21) Appl. No.: 13/877,022

(22) PCT Filed: Jun. 23, 2011

(86) PCT No.: PCT/JP2011/003598
§ 371 (c)(1),
(2), (4) Date: Jun. 18, 2013

(87) PCT Pub. No.: WO2012/042710
PCT Pub. Date: Apr. 5, 2012

(65) Prior Publication Data
US 2013/0310743 A1 Nov. 21, 2013

(30) Foreign Application Priority Data
Sep. 29, 2010 (JP) ................................. 2010-219966

(51) Int. Cl.
*A61M 5/168* (2006.01)

(52) U.S. Cl.
CPC .... *A61M 5/16886* (2013.01); *A61M 5/16836* (2013.01)

(58) Field of Classification Search
CPC .......... A61M 5/16886; A61M 5/16836; A61M 5/16831; A61M 1/1037
See application file for complete search history.

(56) References Cited

U.S. PATENT DOCUMENTS 4,663,032 A * 5/1987 Loos ..................... A61M 1/029
210/513
6,193,480 B1 * 2/2001 Butterfield ........ A61M 5/16831
417/43
(Continued)

FOREIGN PATENT DOCUMENTS

JP 2-224657 A 9/1990
JP 11-137673 A 5/1999
(Continued)

OTHER PUBLICATIONS

Office Action issued on Jun. 18, 2014, by the Japanese Patent Office in corresponding Japanese Patent Application No. 2010-219966. (3 pages).
(Continued)

*Primary Examiner* — Edelmira Bosques
*Assistant Examiner* — Hamza Darb
(74) *Attorney, Agent, or Firm* — Buchanan Ingersoll & Rooney PC

(57) ABSTRACT

An extravasation detecting apparatus is provided which is capable of detecting at an early stage the dislodgment of a tip opening of a solution supplying tool from a blood vessel. The extravasation detecting apparatus includes: a fluid delivery unit which supplies a fluid medicine by repetitively performing operations of pressing and occluding a portion between a fluid medicine containing unit and a puncture site of an infusion tube, subsequently suctioning the fluid medicine from upstream using a restoring force of the infusion tube, and once again pressing and occluding the infusion tube to push out the fluid medicine toward downstream; a tube closing unit located upstream of the fluid delivery unit; and a blood detecting sensor which operates the tube closing unit during a solution supplying operation to generate negative pressure in a downstream infusion tube and which detects whether or not blood is being suctioned between the (Continued)

fluid delivery unit and the puncture site into the infusion tube from a punctured blood vessel.

20 Claims, 30 Drawing Sheets

(56) References Cited

U.S. PATENT DOCUMENTS

| | | | |
|---|---|---|---|
| 7,122,012 | B2 | 10/2006 | Bouton et al. |
| 7,546,776 | B2 | 6/2009 | Ono |
| 2003/0040724 | A1 | 2/2003 | Lynn |
| 2003/0078547 | A1* | 4/2003 | Shekalim .......... A61M 5/16854 604/256 |
| 2004/0225255 | A1* | 11/2004 | Ono ................. A61B 5/0059 604/65 |
| 2006/0167405 | A1* | 7/2006 | King ................. A61M 5/32 604/65 |

FOREIGN PATENT DOCUMENTS

| | | |
|---|---|---|
| JP | 2003-512867 A | 4/2003 |
| JP | 2005-152577 A | 6/2005 |
| JP | 2008-522767 A | 7/2008 |
| JP | 2008-301918 A | 12/2008 |

OTHER PUBLICATIONS

International Search Report (PCT/ISA/210) issued on Jul. 20, 2011, by the Japanese Patent Office as the International Searching Authority for International Application No. PCT/JP2011/003598.

* cited by examiner

F I G. 1
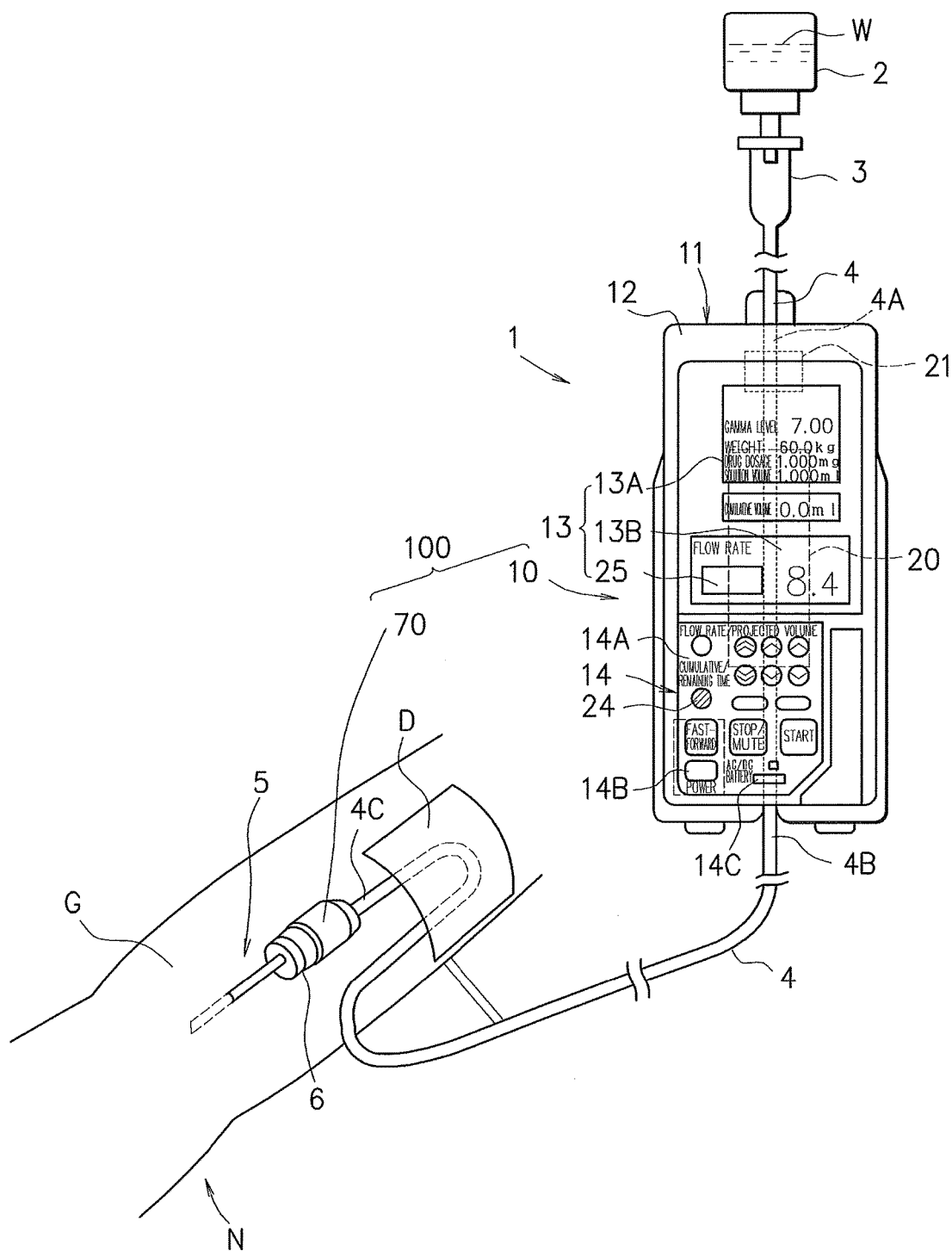

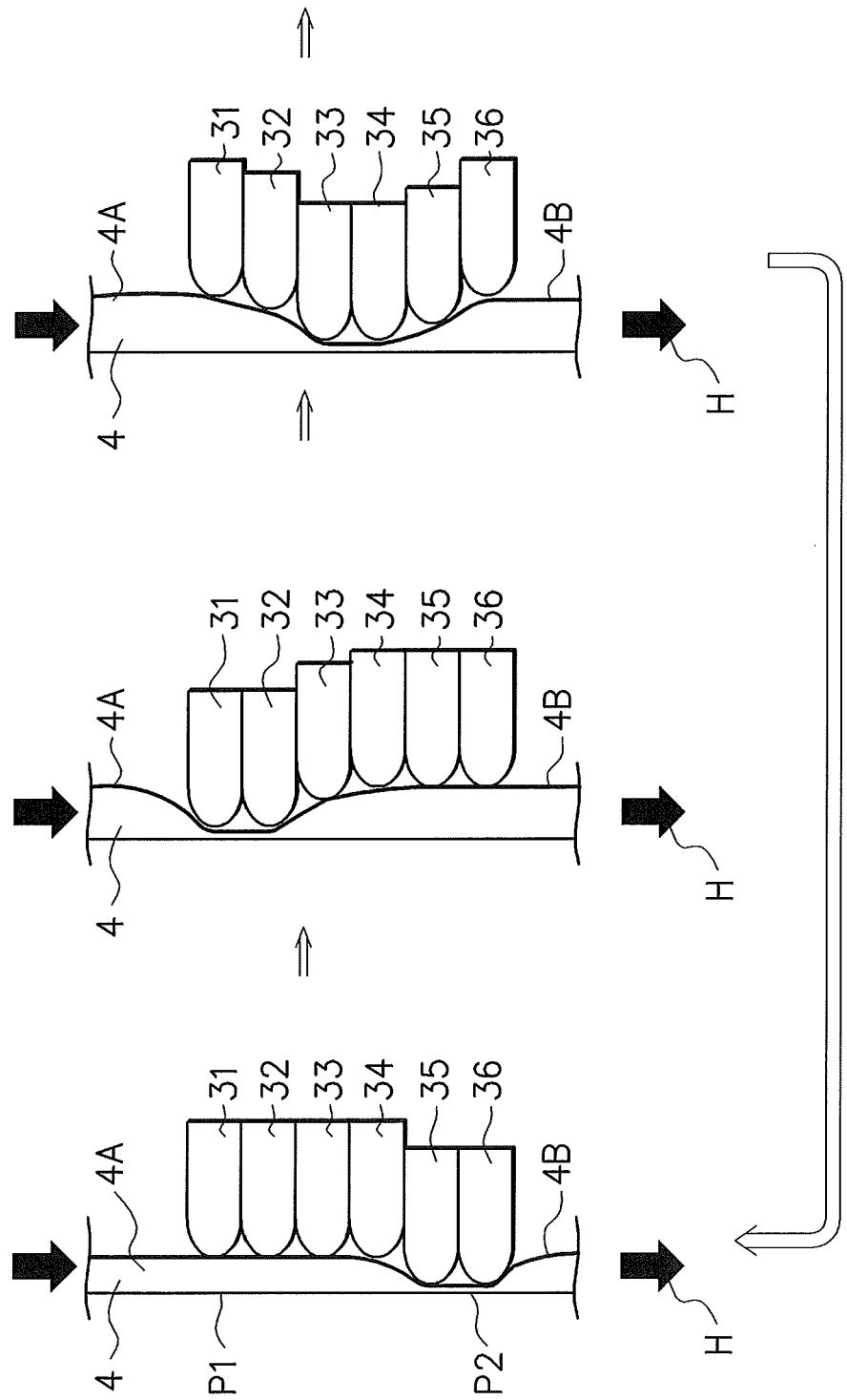

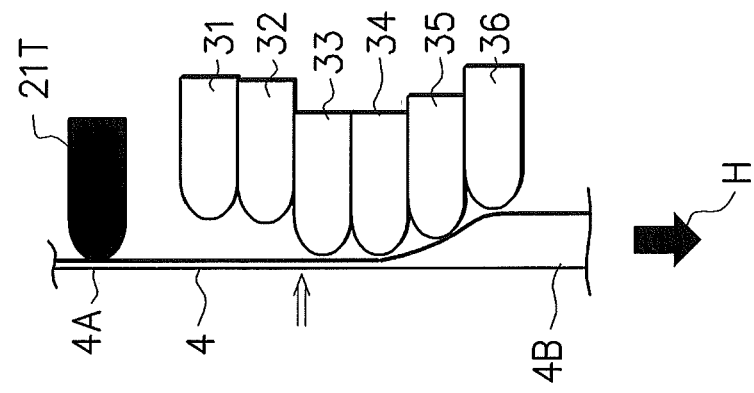
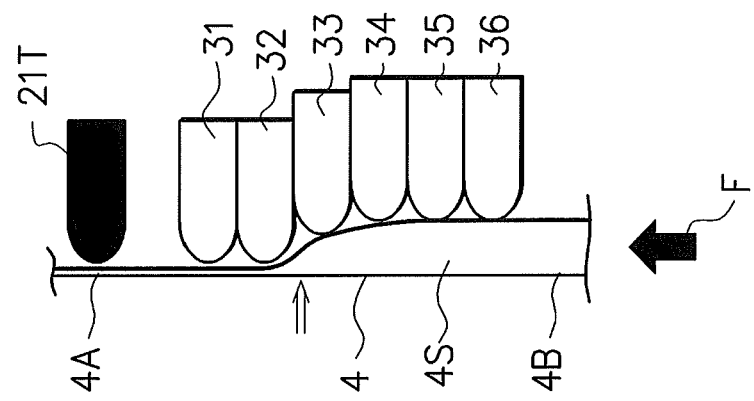
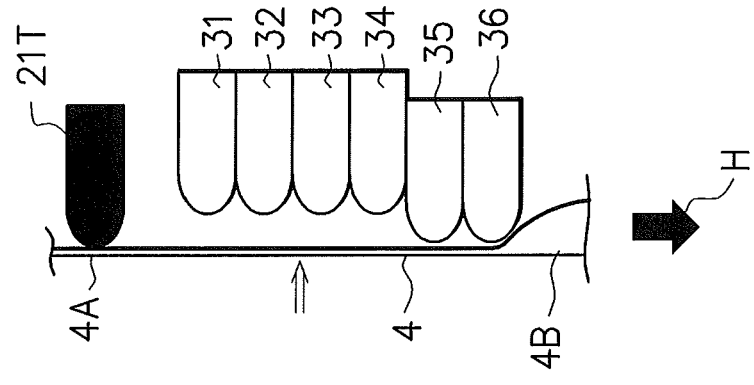

F I G. 5
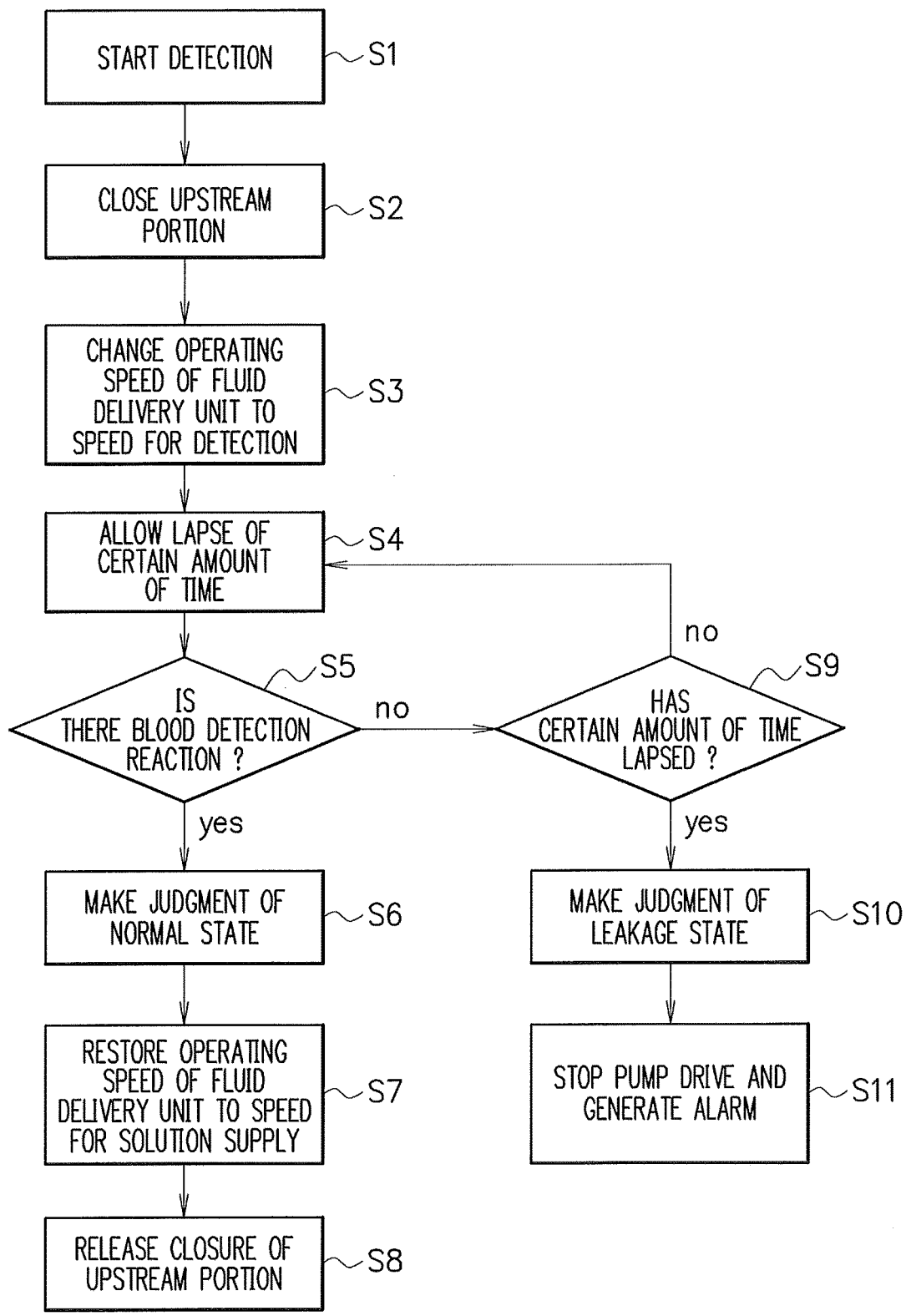

F I G. 6
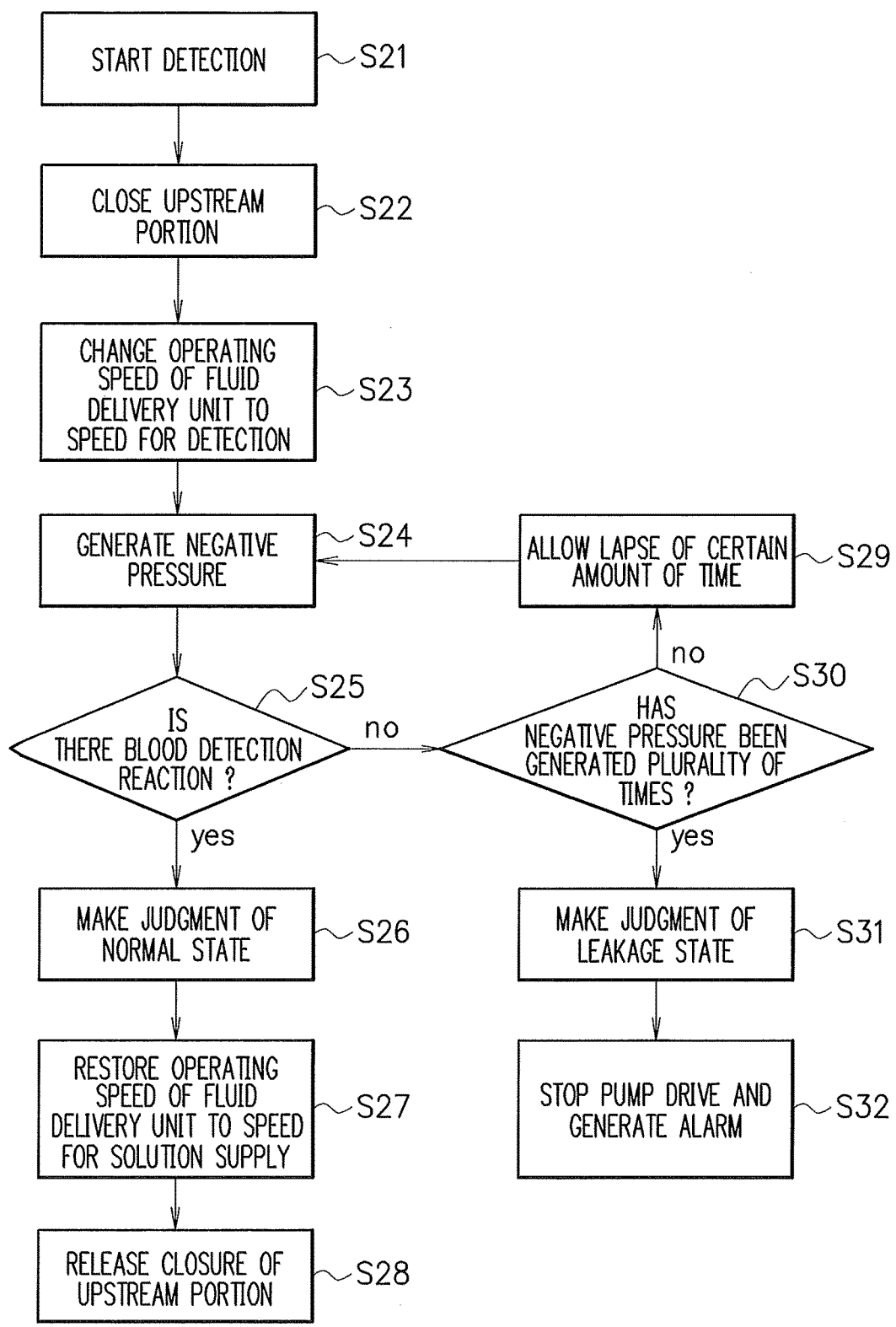

F I G. 7
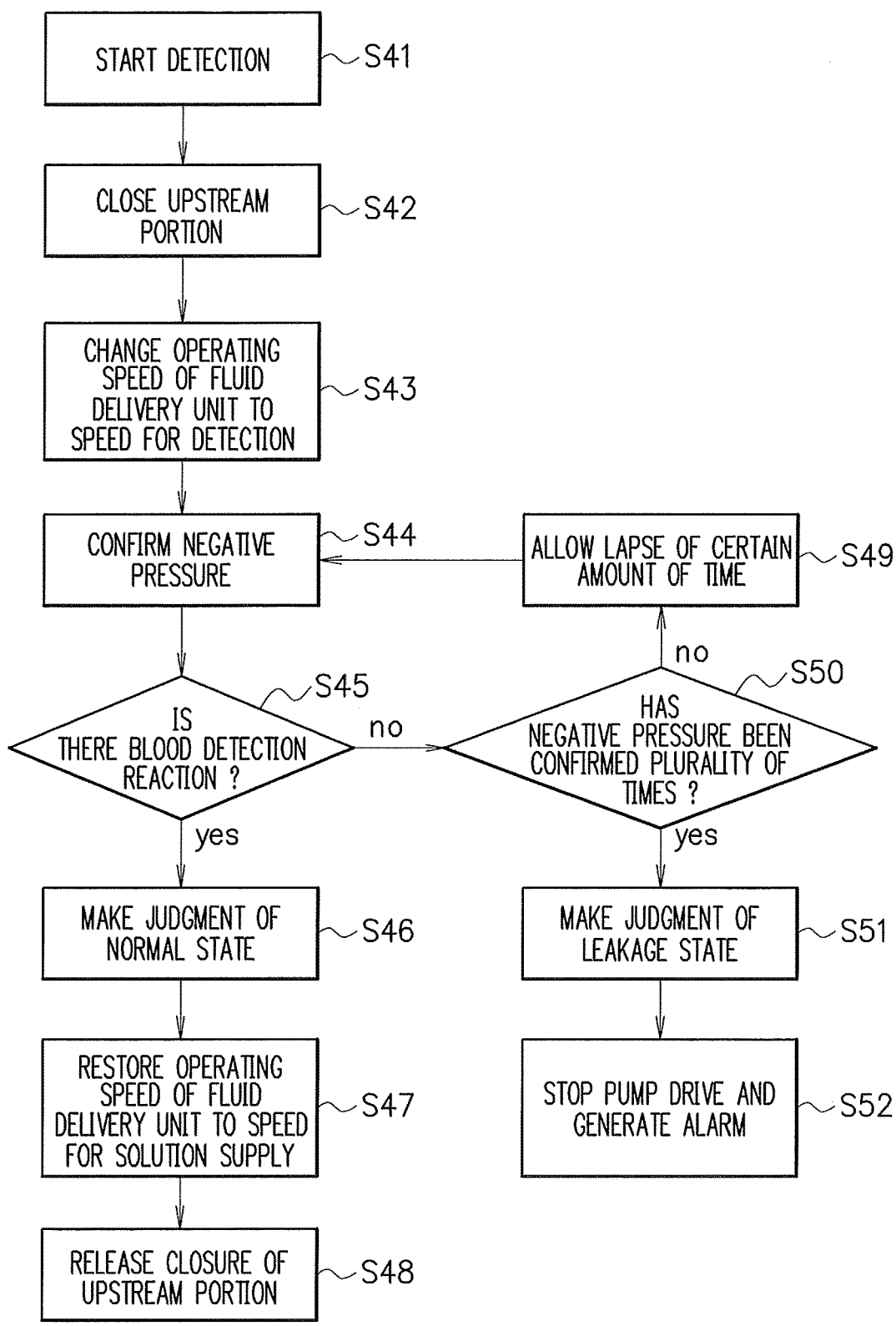

F I G. 30

RELATIONSHIP AMONG INNER DIAMETER OF INFUSION TUBE, BLOOD SUCTION, AND RETURN OF BLOOD

| TUBE INNER DIAMETER | SUCTION OF BLOOD | RETURN OF SUCTIONED BLOOD |
|---|---|---|
| 0.8mm | X | O |
| 1.1mm | X | O |
| 1.5mm | O | O |
| 2.1mm | O | X |
| 3.1mm | O | X |

F I G. 31
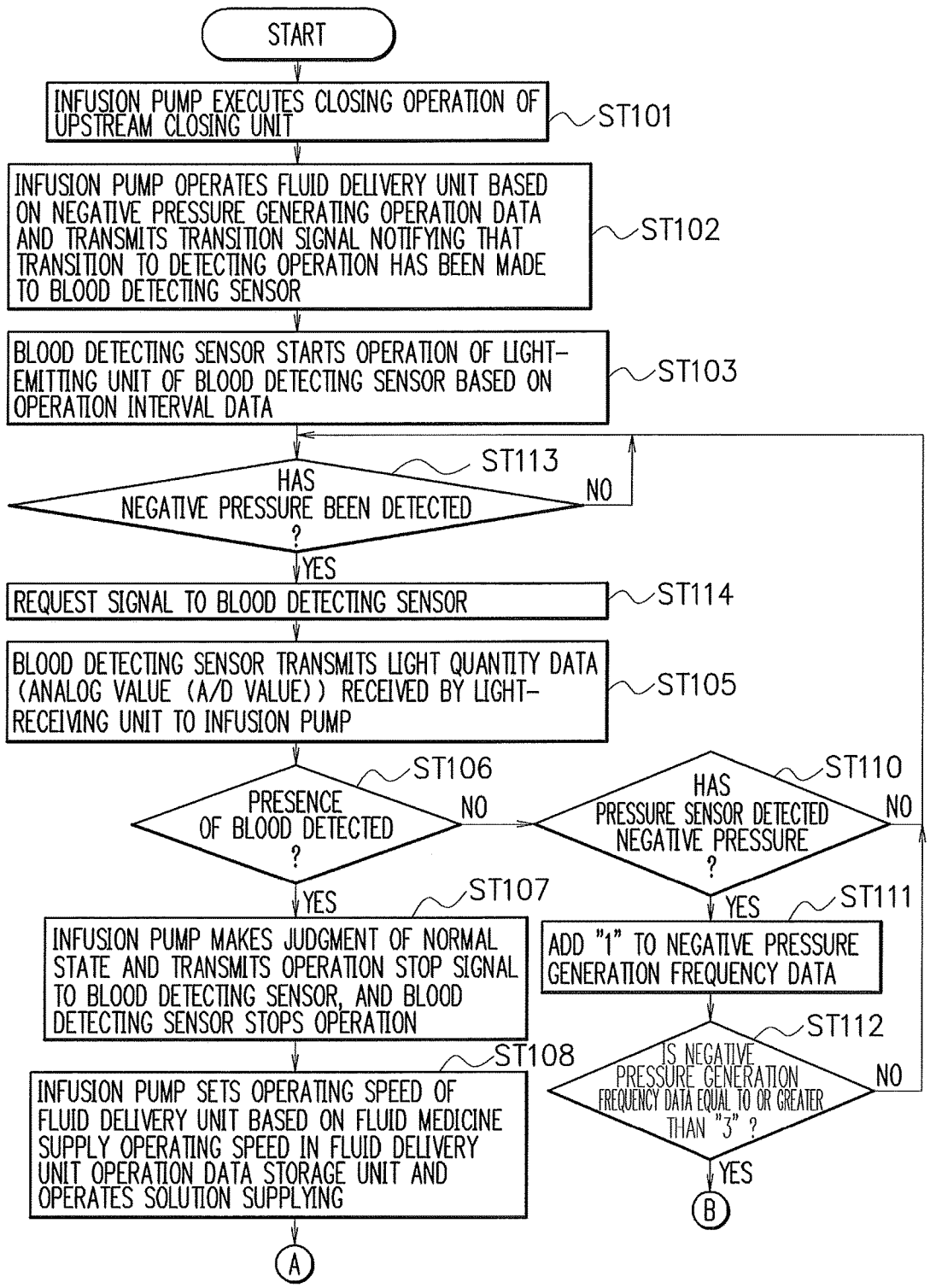

F I G. 32
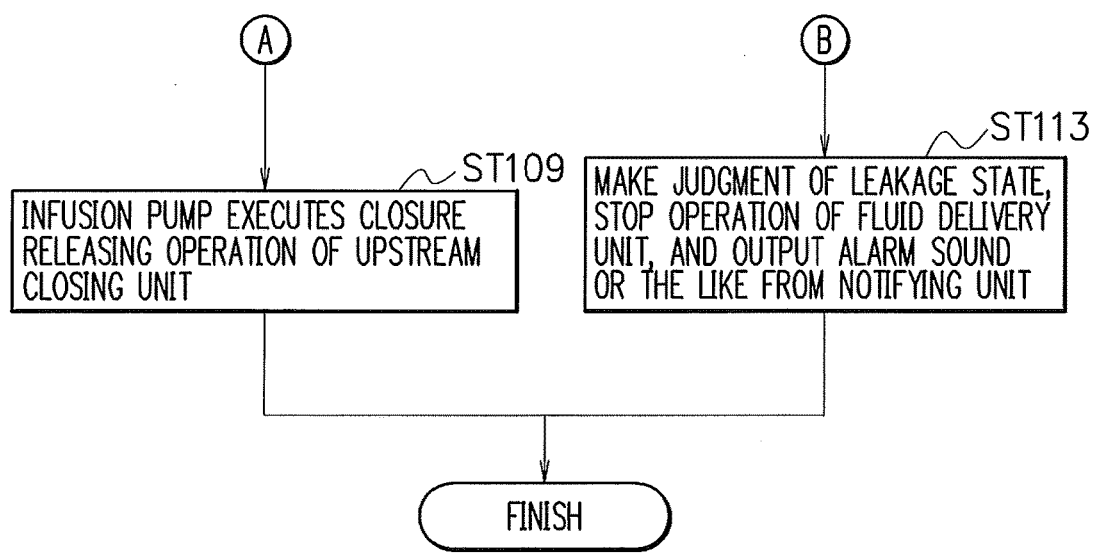

F I G. 35

RELATIONSHIP BETWEEN PUMP FLOW RATE AND
RETURN (DIAMETER 1.5mm)

| FLOW RATE (ml/h) | RETURN OF BLOOD |
|---|---|
| 50 | × |
| 60 | × |
| 70 | ○ |
| 80 | ○ |
| 90 | ○ |
| 100 | ○ |

EXTRAVASATION DETECTING APPARATUS AND INFUSION SYSTEM

TECHNICAL FIELD

The present invention relates to an extravasation detecting apparatus and an infusion system which detect whether or not an indwelling catheter or an indwelling needle is properly placed in a blood vessel and detect a dislodgment of a tip of the indwelling catheter or the indwelling needle from the blood vessel.

BACKGROUND ART

When administering a fluid medicine or the like to a patient by intravenous injection using an indwelling vascular catheter, an indwelling needle, or the like, tension that acts on an infusion tube due to body motion of the patient may cause a tip opening of the indwelling catheter or the indwelling needle to remain in subcutaneous tissue in a state where the tip opening is dislodged from a blood vessel and may result in the fluid medicine leaking into surrounding subcutaneous tissue.

Depending on ingredients of a fluid medicine, leakage of the fluid medicine into surrounding subcutaneous tissue may cause inflammation accompanied by pain in the surrounding subcutaneous tissue and, in extreme cases, may result in necrosis of the tissue. Therefore, it is necessary to detect leakage of the fluid medicine at an early stage and promptly perform treatment involving neutralization and suction of the leaked drug and the use of an anti-inflammatory agent or the like.

In consideration thereof, various types of leakage detecting apparatuses for detecting leakage of a fluid medicine during intravenous injection have been proposed.

Patent Document 1 discloses a method of measuring swelling due to leakage using a change in optical path lengths by sequentially transmitting optical pulse signals (infrared rays) to a skin surface into which an injection needle is inserted and measuring arrival times of optical pulse signals reflected inside a human body.

Patent Document 2 discloses a method which utilizes a principle that a fluid medicine accumulated under the skin due to leakage absorbs microwave and causes the microwave to attenuate, and which checks for leakage based on attenuation by irradiating microwave to an intravenous injection site and measuring the magnitude of reflected waves.

CITATION LITERATURE

Patent Literature

Patent Literature 1: Japanese Patent Application Laid-open No. 2005-152577
Patent Literature 2: U.S. Pat. No. 7,122,012

SUMMARY OF INVENTION

Technical Problem

However, with the leakage detecting methods disclosed in Patent Document 1 and Patent Document 2 described above, leakage is detected based on a change in dimensions of an intravenous injection site due to swelling caused by leakage to the outside of a blood vessel (subcutaneous) or based on the absorption of microwave by a fluid medicine accumulated under the skin as a result of leakage.

These proposals address the detection of secondary phenomena that occur as a result of leakage of a fluid medicine. Therefore, a certain amount of time is required from an occurrence of leakage of the fluid medicine to an occurrence of swelling due to inflammation and, at the same time, a certain amount of the fluid medicine must accumulate in subcutaneous tissue.

Since swelling due to inflammation is yet to occur and only a small amount of the fluid medicine accumulates under the skin immediately after the occurrence of a leakage of the fluid medicine, early detection by these systems is not always successful.

In particular, some anticancer drugs have extremely high drug toxicity, and when leakage of such drugs occurs, even a small amount may result in inflammation or more severe damage to subcutaneous tissue such as necrosis. Therefore, a detection method that enables earliest possible detection is desired.

Furthermore, the leakage detecting methods described above require that a sensor be arranged on a skin surface at a venipuncture site in order to detect leakage of a fluid medicine. However, this means that the skin surface of the puncture site is to be covered by the sensor.

In infusion management, observation of a venipuncture site including occurrences of inflammation due to infection or the like and a state of fixation of a catheter or an infusion tube is important in terms of nursing care. However, the sensor problematically prevents a condition of the skin surface of a puncture site from being visually confirmed.

Therefore, in order to solve the problems described above, it is an object of the present invention to provide an extravasation detecting apparatus and an infusion system which employ a method of directly detecting a tip opening of an indwelling catheter or an indwelling needle having broken out of a blood vessel into subcutaneous tissue instead of employing a method of detecting a secondary change that occurs due to accumulation of leaked fluid medicine under the skin and which is capable of early detection of dislodgment of the tip opening of the indwelling catheter or the indwelling needle from a blood vessel (vein) without having to install a sensor on a puncture site skin surface.

Solution to Problem

In order to achieve the object described above, an extravasation detecting apparatus according to the present invention comprises: a fluid medicine containing unit which contains a fluid medicine and to which a catheter or an indwelling needle to be placed inside a blood vessel is connected by an infusion tube; a fluid delivery unit which supplies the fluid medicine by sequentially and repetitively pressing the infusion tube with a plurality of fingers; an upstream closing unit which is arranged at a portion of the infusion tube upstream the fluid delivery unit and which closes the infusion tube; and a blood detecting sensor which detects whether or not blood is suctioned into the infusion tube from inside the blood vessel upon closing of an upstream portion of the infusion tube by the upstream closing unit when the fluid delivery unit is actuated and negative pressure is generated in the infusion tube by a restoring force of the infusion tube, wherein when the blood detecting sensor detects that blood is being suctioned, a judgment is made that a tip opening of the catheter or the indwelling needle is inside the blood vessel and an extravasation has not occurred, but when the blood detecting sensor detects that blood is not being suctioned, a judgment is made that the tip opening is outside the blood vessel and an extravasation has occurred.

According to the configuration described above, by utilizing a phenomenon that blood is sucked into and returns to the infusion tube when the tip opening of the catheter or the indwelling needle is inside a blood vessel while blood does not return when the tip opening is outside of the blood vessel, dislodgment from the blood vessel and movement in subcutaneous tissue of the tip opening of the catheter or the indwelling needle can be directly detected. Accordingly, unlike a method that requires a certain amount of accumulation in subcutaneous tissue of a drug injected from a tip opening of a catheter or an indwelling needle having entered the subcutaneous tissue or a method that requires a certain amount of time to lapse from a subcutaneous injection of a drug to an occurrence of inflammation followed by swelling, extravasation due to dislodgment of a tip opening of a catheter or an indwelling needle from a blood vessel can be detected at an early stage.

In particular, in a case of infusion treatment using a drug such as anticancer drugs that is likely to cause inflammation, pain, or necrosis when injected into extravascular tissue such as subcutaneous tissue, leakage of a fluid medicine can be discovered at an early stage and damage to surrounding subcutaneous tissue can be kept to a minimum.

In addition, unlike conventional methods, a sensor that carries out detection is arranged in an infusion tube. Therefore, since a sensor need not be arranged on a puncture site of a catheter or an indwelling needle into a human body or on a surrounding skin surface thereof, extravasation can be detected without obstructing observation of the puncture site and the surrounding skin surface by medical personnel.

As shown, with the configuration described above, in case of an operation in which negative pressure is created between the fluid delivery unit of the infusion tube and a blood vessel or, in other words, when blood is suctioned by the fluid delivery unit or by a combination of the fluid delivery unit and the upstream closing unit during supplying of the fluid medicine, blood refluxes from the blood vessel to the infusion tube via a catheter or the like as long as the catheter or the like is appropriately arranged. Extravasation is appropriately detected based on the fact that, on the other hand, if the catheter or the like is not appropriately arranged but is dislodged from the blood vessel, a reflux of blood does not occur even if negative pressure is created between the fluid delivery unit and the blood vessel.

Moreover, in the configuration described above, while a fluid medicine is supplied into a blood vessel of a patient or the like from the fluid medicine containing unit via the infusion tube and the catheter or the like, a solution supplying speed and the like of the fluid medicine is adjusted at the fluid delivery unit.

Preferably, the blood detecting sensor is provided in a vicinity of the catheter or the indwelling needle in order to detect the blood that is suctioned into the infusion tube.

According to the configuration described above, detection can be made even when the amount of blood suctioned by the fluid delivery unit is small.

The blood detecting sensor is provided in a portion having a small inner diameter at a tip portion of the infusion tube.

As shown, the blood detecting sensor is provided in a portion with a small inner diameter at a tip portion of the infusion tube or, in other words, an inner diameter of the tip portion of the infusion tube is set smaller than inner diameters of other portions. In this manner, since the inner diameter of the infusion tube on a side close to a blood vessel is small, a configuration is realized in which blood refluxed from the blood vessel toward the infusion tube is likely to return into the blood vessel when the negative pressure inside the infusion tube or the like is released.

Therefore, even after the negative pressure is released, blood does not remain in the infusion tube and subsequent extravasation detection is not erroneously affected. As a result, dislodgment of a catheter or the like can always be detected at high accuracy.

In other words, when detection of dislodgment of a catheter or the like is performed a plurality of times during administration of an infusion solution, an erroneous judgment due to blood remaining in the infusion tube from a previous detection can be avoided.

Preferably, the blood detecting sensor comprises a light-emitting unit which irradiates light to the suctioned blood, a light-receiving unit which is arranged at a position facing the light-emitting unit across the infusion tube, and a chassis unit which internally contains and holds the light-emitting unit and the light-receiving unit, wherein a light-blocking unit for blocking extraneous light is provided in the chassis unit.

According to the configuration described above, an attenuation of irradiated light due to absorption and reflection of light by blood inside the infusion tube can be detected based on transmitted light whose light quantity is greater than that of reflected light, and detection can be performed with a better SN ratio than when using reflected light.

In addition, by providing the light-blocking unit, an erroneous judgment of a state where there is no return of blood as a result of the light-receiving unit receiving extraneous light that cancels light reduction due to absorption by blood even when there is returning blood can be avoided and blood suctioned into the infusion tube can be reliably detected.

Preferably, the light-emitting unit performs pulsed emission and synchronous detection at a frequency other than 50 Hz, 60 Hz, or a frequency that is a multiple thereof.

According to the configuration described above, the light-receiving unit can perform detection accurately while avoiding a blinking frequency of a light source that is driven by a commercial AC power supply, and extraneous light such as a fluorescent light and light from a light bulb can be eliminated.

Preferably, the blood detecting sensor includes a first antenna unit and a charging unit for feeding power to the light-emitting unit of the blood detecting sensor, the extravasation detecting apparatus further comprises a communication base unit that is separate from the blood detecting sensor, the communication base unit feeds power to the charging unit of the blood detecting sensor by electromagnetic induction with the first antenna unit of the blood detecting sensor, the blood detecting sensor transmits a signal, based on a detection result of a presence or absence of the blood in the infusion tube, from the first antenna unit of the blood detecting sensor to the base unit by wireless communication, and the communication base unit comprises a second antenna unit which notifies to an infusion pump, which includes the fluid delivery unit, of the received signal based on the detection result of the presence or absence of the blood in the infusion tube.

According to the configuration described above, the blood detecting sensor is capable of wirelessly sending and notifying electric energy necessary for operation and a detection signal of the presence or absence of blood to the infusion pump by wireless communication with the communication base unit that is separate from the blood detecting sensor. As a result, downsizing can be achieved since a power supply is no longer necessary, hygienic management of an indwelling site becomes easier since signal lines are not required, and a so-called spaghetti syndrome in which signal lines become intertwined can be reduced.

Preferably, the present invention is an infusion system comprising the solution supplying tool arrangement status detecting apparatus described above.

Advantageous Effects of Invention

According to the present invention, a solution supplying tool arrangement status detecting apparatus, an infusion system, and a solution supplying tool arrangement status detecting method can be provided which are capable of promptly and reliably detecting a dislodgment of a tip opening of a solution supplying tool such as an indwelling catheter or an indwelling needle from a blood vessel (vein) due to body motion of a patient or the like.

BRIEF DESCRIPTION OF DRAWINGS

FIG. 1 is a diagram showing an outline of an infusion system including an embodiment of an extravasation detecting apparatus according to the present invention;

FIGS. 3A-3C are diagrams showing operation examples of supplying a fluid medicine inside an infusion tube by having first to sixth fingers sequentially press the infusion tube from an upstream portion to a downstream portion of the infusion tube;

FIGS. 4A-4C are diagrams showing operation examples of performing suction of blood inside a blood vessel by generating negative pressure inside an infusion tube between an upstream portion and a downstream portion of the infusion tube;

FIG. 5 is a flow diagram showing a first example of an extravasation detecting operation in an infusion system apparatus;

FIG. 6 is a flow diagram showing a second example of an extravasation detecting operation in an infusion system;

FIG. 7 is a flow diagram showing a third example of an extravasation detecting operation in an infusion system;

FIG. 27 is a schematic block diagram showing primary components of a blood detecting sensor shown in FIGS. 20, 21, and the like;

FIGS. 29A and 29B are explanatory schematic diagrams showing a relationship between a diameter of an infusion tube and return of blood, wherein FIG. 29A shows a case of a small diameter infusion tube with an inner diameter of 1.5 mm and FIG. 29B shows a case of a normal diameter infusion tube with an inner diameter of 2 mm;

FIG. 30 is a graph showing a relationship among an inner diameter of an infusion tube, blood suction (during negative pressure), and return of blood;

FIG. 31 is a schematic flow chart showing a first modification of the present embodiment;

FIG. 32 is another schematic flow chart showing the first modification of the present embodiment;

FIG. 35 is a graph showing a relationship between pump flow rate and return (diameter 1.5 mm).

DESCRIPTION OF EMBODIMENTS

Hereinafter, preferred embodiments of the present invention will be described in detail with reference to the drawings.

Figure 2:
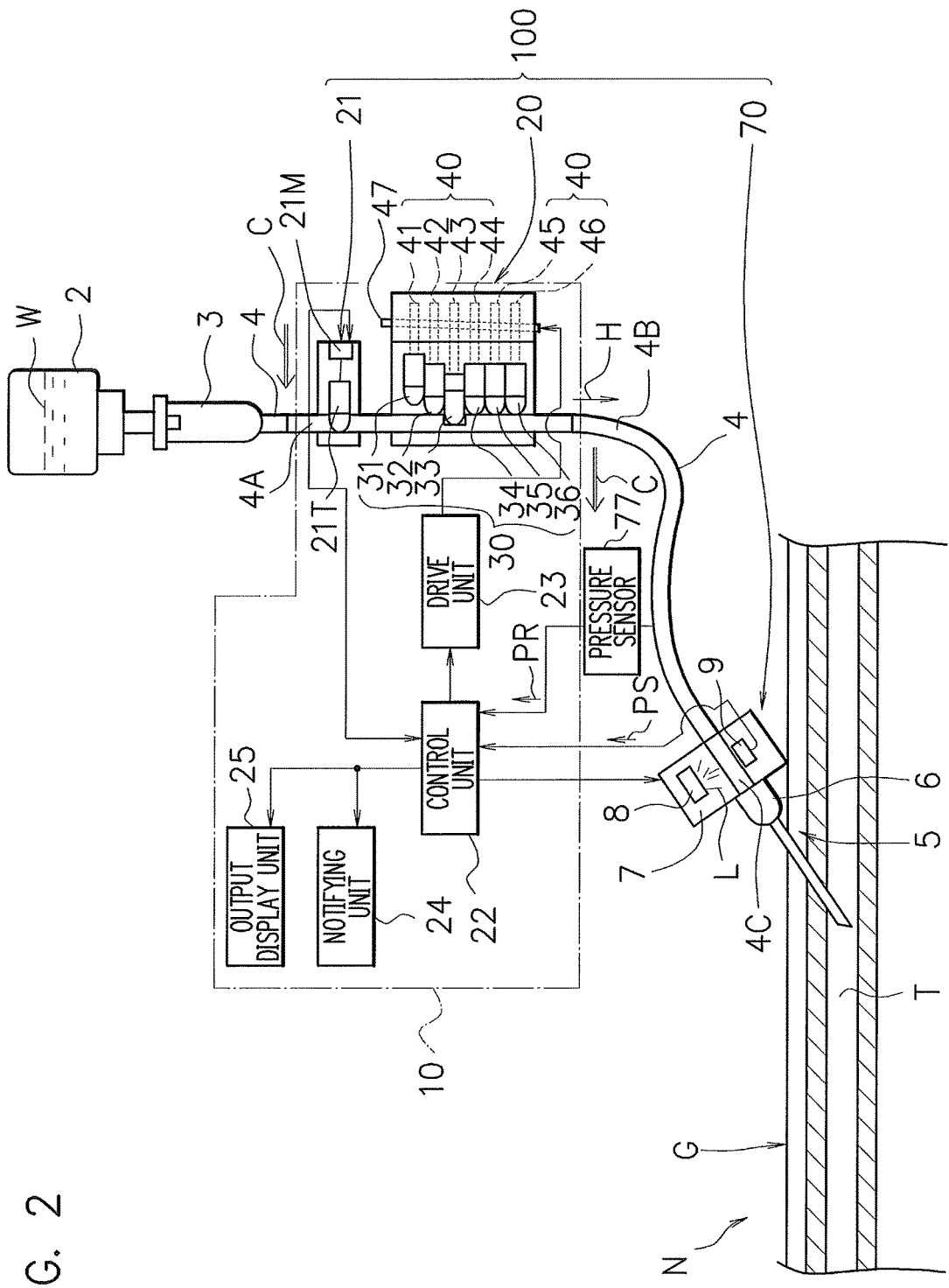
FIG. 2 is a diagram showing a structural example of a part of the infusion system shown in FIG. 1.

FIG. 1 shows an infusion system including an embodiment of an extravasation detecting apparatus according to the present invention. FIG. 2 shows a structural example of the infusion system including the embodiment of the extravasation detecting apparatus shown in FIG. 1.

As shown in FIGS. 1 and 2, an infusion system 1 comprises a fluid medicine bag 2, an instillation unit 3, an infusion pump 10, an infusion tube 4, and an indwelling vascular catheter 5 or an indwelling needle. In this case, an indwelling catheter (hereinafter, simply referred to as a catheter) includes a flexible tube and a junction (hub) which is provided at another end of the flexible tube and which connects the flexible tube with an infusion tube. In addition, an indwelling needle includes a metallic needle formed of stainless steel or the like, a flexible tube connected to the metallic needle, and a junction which is provided at a tip of the flexible tube and which connects the flexible tube with an infusion tube.

As shown in FIG. 1, the fluid medicine bag 2 internally contains a fluid medicine W. The fluid medicine bag 2 is a fluid medicine containing unit which contains the fluid medicine W, and is detachably connected to the instillation unit 3. The instillation unit 3 is integrally connected to one end of the infusion tube 4.

The infusion tube 4 is detachably passed through the infusion pump 10, and another end of the infusion tube 4 is detachably connected to the indwelling catheter (indwelling needle) 5.

The infusion tube 4 is also referred to as an infusion line.

The fluid medicine W inside the fluid medicine bag 2 shown in FIG. 1 enters the infusion tube 4 via the instillation unit 3. Due to a solution supplying operation by the infusion pump 10, the fluid medicine W inside the infusion tube 4 is supplied toward the indwelling catheter (indwelling needle) 5 at a flow rate (mL/h) set for the infusion pump 10.

For example, a vicinity of a connecting portion 4C of the infusion tube 4 on a side of the indwelling catheter 5 is attached to a surface of the skin G of an arm N of a human body by a piece of tape D.

As shown in FIG. 1, the infusion pump 10 comprises a main body 11 and a door 12. The door 12 is mounted to the main body 11 by a hinge and is openable and closable with respect to the main body 11. A display unit 13 and an operating unit 14 are arranged on a surface of the door 12. For example, the display unit 13 is a liquid crystal display panel and comprises a display portion 13A which displays a so-called gamma level and weight and a flow rate display portion 13B which displays a flow rate of the fluid medicine W. The operating unit 14 comprises a flow rate setting button 14A of the fluid medicine W, a power ON/OFF button 14B, a battery display portion 14C, and the like. By opening the door 12 from the main body 11, the infusion tube 4 can be passed into the main body 11 in a longitudinal direction.

FIG. 2 shows elements arranged inside the infusion pump 10 shown in FIG. 1.

The infusion pump 10 comprises a fluid delivery unit 20, an upstream closing unit 21, a control unit 22 which is constituted by a RAM, a ROM, and a microcomputer and which includes a judging unit and controls the entire apparatus, a drive unit 23, a notifying unit 24, and an output display unit 25.

The fluid delivery unit 20, the upstream closing unit 21, the control unit 22, and the drive unit 23 are arranged inside the main body 11 shown in FIG. 1.

For example, the notifying unit 24 is arranged in the operating unit 14 of the door 12 shown in FIG. 1.

For example, the output display unit 25 is arranged in the display unit 13 of the door 12 shown in FIG. 1.

Returning to FIG. 2, the control unit 22 is electrically connected to the drive unit 23, the notifying unit 24, and the output display unit 26.

The notifying unit 24 may adopt at least one of a speaker which provides audio guidance, a buzzer which performs audio notifications, a lamp which performs optical notifications, and the like.

As shown in FIG. 2, the upstream closing unit 21 is arranged between the instillation unit 3 and the fluid delivery unit 20 and is provided in order to close an upstream portion 4A of the infusion tube 4 between the instillation unit 3 and the fluid delivery unit 20.

The infusion tube 4 is made of a thermoplastic resin which is flexible and highly restorative, and is translucent.

The upstream closing unit 21 comprises a pressing member 21T and an actuator 21M. The actuator 21M is electrically connected to the control unit 22.

In response to an instruction issued by the control unit 22, the actuator 21M is capable of almost completely closing the upstream portion 4A of the infusion tube 4 by moving the pressing member 21T in a C direction toward the upstream portion 4A of the infusion tube 4.

In addition, since the upstream portion 4A of the infusion tube 4 can be opened by actuating the actuator 21M in reverse, the upstream portion 4A can be restored to once again pass the fluid medicine W through. The C direction is a direction that is perpendicular to an axial direction of the infusion tube 4.

A configuration of the fluid delivery unit will be described with reference to FIG. 2.

As shown in FIG. 2, the drive unit 23 is, for example, an electric motor and is driven according to an instruction issued by the control unit 22.

The fluid delivery unit 20 comprises the drive unit 23 and a pump mechanism unit 30.

The pump unit 30 is arranged on a downstream side of the upstream closing unit 21 and comprises a plurality of fingers such as first to sixth fingers 31 to 36 and an operating cam unit 40.

While an example having six fingers is illustrated, the number of fingers can be arbitrarily selected.

The fluid delivery unit 20 employs a peristaltic system in which the infusion tube 4 is sequentially pressed by the first to sixth fingers 31 to 36 to be completely occluded. A solution supplying system which does not completely occlude the infusion tube 4 may be employed instead.

The first to sixth fingers 31 to 36 shown in FIG. 2 are arranged stacked in an H direction from the upstream portion 4A to the downstream portion 4B along the infusion tube 4. The operating cam unit 40 includes first to sixth cam surface portions 41 to 46. The first to sixth cam surface portions 41 to 46 are respectively arranged so as to correspond to the first to sixth fingers 31 to 36.

The first to sixth cam surface portions 41 to 46 are fixed to a shaft portion 47 and have cam follower surfaces that differ from each other. Due to the drive unit 23 rotating the shaft portion so that the first to sixth cam surface portions 41 to 46 respectively move in a C direction in a sequence of corresponding first to sixth fingers 31 to 36 according to an order to be described later, a position where the infusion tube 4 is occluded can be varied.

A principle of supplying a solution by the fluid delivery unit 20 of the peristaltic infusion pump 10 described earlier with reference to FIGS. 3 and 4 and a principle of generating negative pressure by operating the fluid delivery unit 20 in a state where an upstream side is closed by the upstream closing unit 21 will now be described.

First, the principle of the fluid delivery unit will be described with reference to FIG. 3.

FIG. 3 shows an operation example of fingers supplying a fluid medicine inside the infusion tube 4 at a set flow rate (mL/h) by having the first to sixth fingers 31 to 36 sequentially press and occlude the infusion tube 4 from the upstream portion 4A to the downstream portion 4B of the infusion tube 4 in the peristaltic infusion pump 10 described above.

A solution supplying operation will now be described with reference to FIG. 3.

FIGS. 3A, 3B, and 3C respectively show states of the first to sixth fingers 31 to 36 when a solution supplying operation by the fluid delivery unit 22 of the infusion pump 10 is being performed or stopped. The following description of the solution supplying operation will be centered on the state shown in FIG. 3A.

In FIG. 3A, a fluid medicine is injected into the infusion tube 4 from the upstream portion 4A in a state where the infusion tube 4 is completely occluded by the fingers 35 and 36.

As a camshaft rotates, a cam causes the finger 35 to return while leaving the finger 36 as-is, and the finger 31 is gradually pushed out. After regions P1 and P2 of the infusion tube 4 enter an occluded state, the finger 36 returns while the finger 31 is left as-is, and the finger 32 is gradually pushed out to create a state shown in FIG. 3B.

Subsequently, the finger 31 returns while the finger 32 is left as-is, and the finger 33 is gradually pushed out. The infusion tube 4 is occluded by the fingers 32 and 33. At this point, the fluid medicine is replenished from the upstream portion 4A to a location that is restored due to the return of the finger 31 while the fluid medicine existing in a region that is occluded by the finger 33 is pushed out into the downstream portion 4B.

Subsequently, the finger 32 returns while the finger 33 is left as-is, and the finger 34 is gradually pushed out. The infusion tube 4 is occluded by the fingers 33 and 34 to create a state shown in FIG. 3C.

Subsequently, the finger 33 returns while the finger 34 is left as-is, and the finger 35 is gradually pushed out. The infusion tube 4 is occluded by the fingers 34 and 35.

Subsequently, the finger 34 returns while the finger 35 is left as-is, and the finger 36 is gradually pushed out. The infusion tube 4 is occluded by the fingers 35 and 36 to create a state shown in FIG. 3A. The phases above are repeated.

With the above constituting a single cycle of the fingers, an internal volume from P1 to P2 shown in FIG. 3A of the infusion tube 4 is supplied from the downstream portion 4B.

The control unit 22 shown in FIG. 2 adjusts a flow rate of an infusion solution by changing the number of strokes per unit time with the internal volume described above corresponding to a single stroke.

Next, the principle of generating negative pressure by operating the fluid delivery unit 20 in a state where the upstream portion 4A is closed by the upstream closing unit 21 will be described with reference to FIG. 4.

When fingers move from the state shown in FIG. 3B with the upstream portion 4A occluded and a state is reached where the infusion tube 4 is completely occluded by the fingers 5 and 36 as shown in FIG. 4A via the state shown in FIG. 3C, the fluid medicine is not injected into the infusion tube from the upstream portion 4A and the infusion tube 4 remains in a squashed state. Subsequently, the camshaft rotates and the cam causes the finger 35 to return while leaving the finger 36 as-is, and the finger 31 is gradually pushed out. After regions P1 and P2 of the infusion tube 4 enter an occluded state, the finger 36 returns while the finger 31 is left as-is, and the finger 32 is gradually pushed out to create a state shown in FIG. 4B. When this state is reached, the squashed infusion tube 4 is restored and the fluid medicine is rapidly suctioned by the downstream portion 4B. Due to this phenomenon, the inside of the infusion tube 4 at the downstream portion 4B rapidly assumes negative pressure and blood is swiftly suctioned by a tip opening 5A of the catheter or the indwelling needle.

Subsequently, the finger 31 returns while the finger 32 is left as-is, and the finger 33 is gradually pushed out. The infusion tube 4 is occluded by the fingers 32 and 33.

At this point, while the fluid medicine existing in a region occluded by the finger 33 is pushed out into the downstream portion 4B, the fluid medicine is not replenished at a location that is restored by the return of the finger 31 since the upstream portion 4A is further closed and the location remains in a squashed state.

Subsequently, the finger 32 returns while the finger 33 is left as-is, and the finger 34 is gradually pushed out. The infusion tube 4 is occluded by the fingers 33 and 34 to create a state shown in FIG. 4C.

Subsequently, the finger 33 returns while the finger 34 is left as-is, and the finger 35 is gradually pushed out. The infusion tube 4 is occluded by the fingers 34 and 35.

Subsequently, the finger 34 returns while the finger 35 is left as-is, and the finger 36 is gradually pushed out. The infusion tube is occluded by the fingers 35 and 36 to create a state shown in FIG. 4A and a volume suctioned into the infusion tube 4 is restored. The phases above are repeated.

Blood that is swiftly suctioned is not returned into a blood vessel with a gentle pressing force of the fingers and remains, and when swiftly suctioned once again, the remaining blood is gradually transferred to the side of the infusion pump 10.

As described above, by repeating the operations shown in FIGS. 4A to 4C, periodic suction operations can be performed.

Next, an extravasation detecting apparatus 100 will be described with reference to FIG. 2.

The extravasation detecting apparatus 100 comprises the upstream closing unit 21 and the fluid delivery unit 20 of the infusion pump 10 and a blood detecting sensor 70.

The extravasation detecting apparatus 100 is used to detect a dislodgment of the tip opening 5A of the catheter 5 from the blood vessel T instead of detecting an accumulation in subcutaneous tissue of a fluid medicine leaking from the catheter 5. By detecting that the tip opening 5A of the catheter 5 has been dislodged from the blood vessel T, a possibility that the fluid medicine has leaked out into surrounding subcutaneous tissue of the skin G can be notified.

As shown in FIG. 2, for example, the blood detecting sensor 70 is arranged in a vicinity of the catheter 5. In addition, for example, the blood detecting sensor 70 is fixed at a connecting portion 4C of the infusion tube 4 in a vicinity of a hub 6 of the catheter 5. Since only a limited amount of blood can be suctioned at one time with the suction method described above, the blood sensor 70 is desirably arranged in close proximity to the catheter 5. FIGS. 1 and 2 show a state where the tip opening 5A of the catheter 5 is inserted into a blood vessel (vein) T of the skin G of an arm N of a human body or, in other words, a state where infusion is normally performed.

As shown in FIG. 2, for example, the blood detecting sensor 70 comprises a ring-like main body unit 7, a light-emitting unit 8, and a light-receiving unit 9. The light-emitting unit 8 preferably generates infrared rays. In order to enable light L emitted by the light-emitting unit 8 to pass through a portion of the infusion tube 4 through which a fluid medicine or blood passes and to be received by the light-receiving unit 9, the light-emitting unit 8 and the light-receiving unit 9 are arranged so as to oppose each other across the infusion tube 4 on the outside of the infusion tube 4.

For example, a light-emitting diode, a laser diode, or the like can be used as the light-emitting unit 8. For example, a photodiode, a phototransistor, and the like can be used as the light-receiving unit 9. In response to an instruction issued by the control unit 22, the light-emitting unit 8 performs pulsed emission at a frequency other than 50 Hz, 60 Hz, or a frequency that is a multiple thereof and the light-receiving unit 9 detects a variable component of received light quantity synchronized with the frequency of the light emitted by the light-emitting unit 8. Accordingly, the light-receiving unit can perform detection accurately while avoiding a blinking frequency of a light source that is driven by a commercial AC power supply, and extraneous light such as a fluorescent light and light from a light bulb can be eliminated.

The light-emitting unit 8 generates infrared rays in response to a signal from the control unit 22. The light-receiving unit 9 converts the received light L into an electric signal and sends the electric signal to the control unit 22 as a light reception signal PS. Based on a reduction of received light quantity of the light L (infrared rays) at the light-receiving unit 9 caused by the infrared rays being blocked by blood passing through the infusion tube 4, a passage of blood through the connecting portion 4C of the infusion tube 4 can be detected.

Next, first to third examples of extravasation detecting operations that can be performed by the infusion system 1 comprising the extravasation detecting apparatus 100 above will be described.

First Example of Extravasation Detecting Operation

FIG. 5 is a flow diagram showing a first example of an extravasation detecting operation by the infusion system 1.

The first example of extravasation detecting operation will now be described with reference to FIG. 5.

The first example of extravasation detecting operation comprises steps S1 to S11. In step S1, during an infusion operation of the fluid medicine W shown in FIG. 2, an infusion operation mode is switched to an extravasation confirmation mode to start detection of blood. In step S2, by moving the pressing member 21T of the upstream closing unit 21 shown in FIG. 2 in a C direction toward the upstream portion 4A of the infusion tube 4, the upstream portion 4A of the infusion tube 4 is squashed and closed as shown in FIG. 4.

In step S3 shown in FIG. 5, when necessary, an operating speed of the first to sixth fingers 31 to 36 of the fluid delivery unit 20 is changed from a normal speed for solution supplying (a speed corresponding to an initially set flow rate (mL/h)) to a speed for extravasation detection of blood. In this case, the first to sixth fingers 31 to 36 can suction blood inside the blood vessel T from a tip opening of the catheter 5 by generating negative pressure in the infusion tube 4 through a negative pressure generating operation shown in FIGS. 4A to 4C. Moreover, an operating speed of the first to sixth fingers 31 to 36 for normal solution supplying is determined based on a fluid velocity of an infusion solution.

In step S4 to which a transition is made from step S3 or step S9, a certain amount of time lapses before a transition is made to step S5. In step S5, during the certain amount of time required by the transition from step S4, if the blood detecting sensor 70 shown in FIG. 2 has detected blood at the connecting portion 4C of the infusion tube 4 and has given a detection signal PS to the control unit 22, in step S6, the control unit 22 judges that the tip opening 5A of the catheter 5 is normally inserted into the blood vessel T as shown in FIG. 2. In step S7, the operating speed of the first to sixth fingers 31 to 36 of the fluid delivery unit 20 is restored from the speed for extravasation detection of blood to the normal speed for solution supplying. Subsequently, in step S8, the pressing member 21T of the upstream closing unit 21 shown in FIG. 2 is restored in a direction opposite to the C direction to release the closure of the upstream portion 4A of the infusion tube 4 and restart infusion of the fluid medicine.

In this case, the certain amount of time in step S4 described above is an amount of time that is required for one repetition of A to C in FIG. 4 and is determined according to the operating speed of the first to sixth fingers 31 to 36 of the fluid delivery unit 20.

In step S5, when the blood detecting sensor 70 shown in FIG. 2 is unable to detect blood at the connecting portion 4C of the infusion tube 4, the control unit 22 stands by for a certain amount of time or longer in step S9, and in step S10, the control unit 22 judges that a state exists where the tip opening 5A of the catheter 5 is not normally inserted into the blood vessel T as shown in FIG. 2 but is dislodged from the blood vessel T and the fluid medicine is leaking out from the blood vessel.

Subsequently, in step S11, the control unit 22 shown in FIG. 2 stops driving of the infusion pump 10, uses the notifying unit 24 shown in FIG. 2 to issue a notification to a patient or medical personnel by means of a buzzer sound, an audio announcement, or a warning light and to generate an alarm, and provides an alarm display on the output display unit 25.

Accordingly, by detecting that the tip opening 5A of the catheter 5 is dislodged from a blood vessel, medical personnel can visually or audibly confirm a possibility that leakage of the fluid medicine has occurred.

In this case, the certain amount of time in step S9 described above is an amount of time that lapses after closing the upstream side 4A of the infusion tube 4 by the upstream closing unit 21 and is an amount of time that is required for a predetermined number of repetitions such as three or four repetitions of A to C in FIG. 4. Therefore, the certain amount of time in step S9 described above is determined according to the operating speed of the first to sixth fingers 31 to 36 of the fluid delivery unit 20.

Second Example of Extravasation Detecting Operation

Next, FIG. 6 is a flow diagram showing a second example of an extravasation detecting operation by the infusion system 1.

The second example of extravasation detecting operation will now be described with reference to FIG. 6.

The second example of extravasation detecting operation is based on the premise that a movement status of the first to sixth fingers 31 to 36 engaged in pressing during an operation of the infusion tube 4 can be known or, in other words, a timing where the state shown in FIG. 4A is created from an operation of the infusion pump 10 or a timing where negative pressure is generated in the infusion tube 4 can be known.

The second example of extravasation detecting operation comprises steps S21 to S32. In step S21, during an infusion operation of the fluid medicine W shown in FIG. 2, an infusion operation mode is switched to an extravasation confirmation mode to start detection of blood. In step S22, by moving the pressing member 21T of the upstream closing unit 21 shown in FIG. 2 in a C direction toward the upstream portion 4A of the infusion tube 4, the upstream portion 4A of the infusion tube 4 is pressed and closed as shown in FIG. 4. A timing where the upstream portion 4A is closed is optimally immediately after the first finger 31 that is furthest upstream among the first to sixth fingers 31 to 36 for solution supplying has been pushed out.

In step S23, when necessary, an operating speed of the first to sixth fingers 31 to 36 of the fluid delivery unit 20 is changed from a normal speed for solution supplying (a speed corresponding to an initially set flow rate (mL/h)) to a speed for extravasation detection of blood. In this case, the first to sixth fingers 31 to 36 cause a part of the blood inside the blood vessel T to be suctioned from the tip opening 5A of the catheter 5 by generating negative pressure in the infusion tube 4 through a negative pressure generating operation shown in FIGS. 4A to 4C. A normal operating speed of the first to sixth fingers 31 to 36 is determined based on a fluid velocity of the infusion solution.

In step S24, when the first to sixth fingers 31 to 36 of the infusion pump 10 are operated until a timing where negative pressure is generated in the infusion tube 4 and negative pressure is generated, in step S25, if the blood detecting sensor 70 shown in FIG. 2 has detected blood at the connecting portion 4C of the infusion tube 4 and has given a detection signal PS to the control unit 22, in step S26, the control unit 22 judges that the tip opening of the catheter 5 is normally inserted into the blood vessel T as shown in FIG. 2. In step S27, the operating speed of the first to sixth fingers 31 to 36 of the fluid delivery unit 20 is restored from the speed for extravasation detection of blood to the normal speed for solution supplying. Subsequently, in step S28, 5A restores the pressing member 21T of the upstream closing unit 21 shown in FIG. 2 in a direction opposite to the C direction to release the closure of the upstream portion 4A of the infusion tube 4 and restart supplying of the fluid medicine.

On the other hand, in step S25, when the blood detecting sensor 70 shown in FIG. 2 is unable to detect blood at the connecting portion 4C of the infusion tube 4, if negative pressure has not been generated a plurality of times in a space 4S of the infusion tube 4 in step S30, a transition is made to step S29. In step S29, a transition is made to step S24 after a lapse of a certain amount of time to wait for a timing where negative pressure is generated and suction can be restarted and to wait to see whether or not the blood detecting sensor 70 can obtain a blood detection reaction.

In this case, the certain amount of time in step S24 described above is an amount of time that is shorter than an amount of time required for one repetition of A to C in FIG. 4 and is determined according to the operating speed of the first to sixth fingers 31 to 36 of the fluid delivery unit 20.

In step S30, when negative pressure has already been generated a plurality of times such as two or three times, a transition is made to step S31 and the control unit 22 judges that a state exists where the tip opening 5A of the catheter 5 is not normally inserted into the blood vessel T as shown in FIG. 2 but is dislodged from the blood vessel T and the fluid medicine is leaking out from the blood vessel. Subsequently, in step S32, the control unit 22 shown in FIG. 2 stops driving of the infusion pump 10, uses the notifying unit 24 shown in FIG. 2 to issue a notification to a patient or medical personnel by means of a buzzer sound, an audio announcement, or a warning light and to generate an alarm, and provides an alarm display on the output display unit 25.

Accordingly, by detecting that the tip opening 5A of the catheter 5 is dislodged from a blood vessel, medical personnel can visually or audibly confirm a possibility that leakage of the fluid medicine has occurred.

Third Example of Extravasation Detecting Operation

Next, FIG. 7 is a flow diagram showing a third example of an extravasation detecting operation by the infusion system 1.

The third example of extravasation detecting operation will now be described with reference to FIG. 7.

The third example of extravasation detecting operation is based on the premise that pressure inside the infusion tube 4 can be detected. In this case, as illustrated in FIG. 2, a pressure sensor 77 is connected to the infusion tube 4, and a pressure signal PR inside the infusion tube 4 that is obtained by the pressure sensor 77 is given to the control unit 22.

The second example of extravasation detecting operation comprises steps S41 to S52. In step S41, during an infusion operation of the fluid medicine W shown in FIG. 2, an infusion operation mode that is performed at a normal speed for solution supplying (a speed corresponding to an initially set flow rate (mL/h)) is switched to an extravasation confirmation mode to start detection of blood. In step S42, by moving the pressing member 21T of the upstream closing unit 21 shown in FIG. 2 in a C direction toward the upstream portion 4A of the infusion tube 4, the upstream portion 4A of the infusion tube 4 is squashed and closed as shown in FIG. 4.

In step S43, when necessary, an operating speed of the first to sixth fingers 31 to 36 of the fluid delivery unit 20 is changed from a normal speed for solution supplying to a speed for extravasation detection of blood. In this case, the first to sixth fingers 31 to 36 cause a part of the blood inside the blood vessel T to be suctioned from the tip opening 5A of the catheter 5 by generating negative pressure in the infusion tube 4 through a negative pressure generating operation shown in FIGS. 4A to 4C. A normal operating speed of the first to sixth fingers 31 to 36 is determined based on a fluid velocity of the infusion solution.

In step S44, the control unit 22 confirms that negative pressure has been created inside the infusion tube 4 based on the pressure signal PR of the pressure sensor 77. Subsequently, in step S45, if the blood detecting sensor 70 shown in FIG. 2 has detected blood at the connecting portion 4C of the infusion tube 4 and has given a detection signal PS to the control unit 22, in step S46, the control unit 22 judges that the tip opening 5A of the catheter 5 is normally inserted into the blood vessel T as shown in FIG. 2.

In step S47, the operating speed of the first to sixth fingers 31 to 36 of the fluid delivery unit 20 is restored from the speed for extravasation detection of blood to the normal speed for solution supplying. Subsequently, in step S48, the pressing member 21T of the upstream closing unit 21 shown in FIG. 2 is restored in a direction opposite to the C direction to release the closure of the upstream portion 4A of the infusion tube 4 and restart infusion of the fluid medicine.

In step S45, when the blood detecting sensor 70 shown in FIG. 2 is unable to detect blood at the connecting portion 4C of the infusion tube 4, if negative pressure has not been generated a plurality of times in the space 4S of the infusion tube 4 in step S50, a transition is made to step S49. In step S29, a transition is made to step S44 after a lapse of a certain amount of time to wait for a timing where negative pressure is generated and suction can be restarted and to wait to see whether or not the blood detecting sensor 70 can obtain a blood detection reaction.

In this case, the certain amount of time in step S44 described above is an amount of time that is shorter than an amount of time required for one repetition of A to C in FIG. 4 and is determined according to the operating speed of the first to sixth fingers 31 to 36 of the fluid delivery unit 20.

In step S50, when negative pressure has been generated a plurality of times such as two or three times, a transition is made to step S51 and the control unit 22 judges that a state exists where the tip opening 5A of the catheter 5 is not normally inserted into the blood vessel T as shown in FIG. 2 but is dislodged from the blood vessel T and the fluid medicine is leaking out from the blood vessel. Subsequently, in step S52, the control unit 22 shown in FIG. 2 stops driving of the infusion pump 10, uses the notifying unit 24 shown in FIG. 2 to issue a notification to a patient or medical personnel by means of a buzzer sound, an audio announcement, or a warning light and to generate an alarm, and provides an alarm display on the output display unit 25.

Accordingly, by detecting that the tip opening 5A of the catheter 5 is dislodged from a blood vessel, medical personnel can visually or audibly confirm a possibility that leakage of the fluid medicine has occurred and take appropriate measures with respect to the leakage of the fluid medicine.

Next, output from the blood detecting sensor 70 and a situation where pressure inside the infusion tube 4 changes when performing an animal experiment using the infusion system 1 above will be described with reference to FIGS. 8 to 10.

Figure 8:
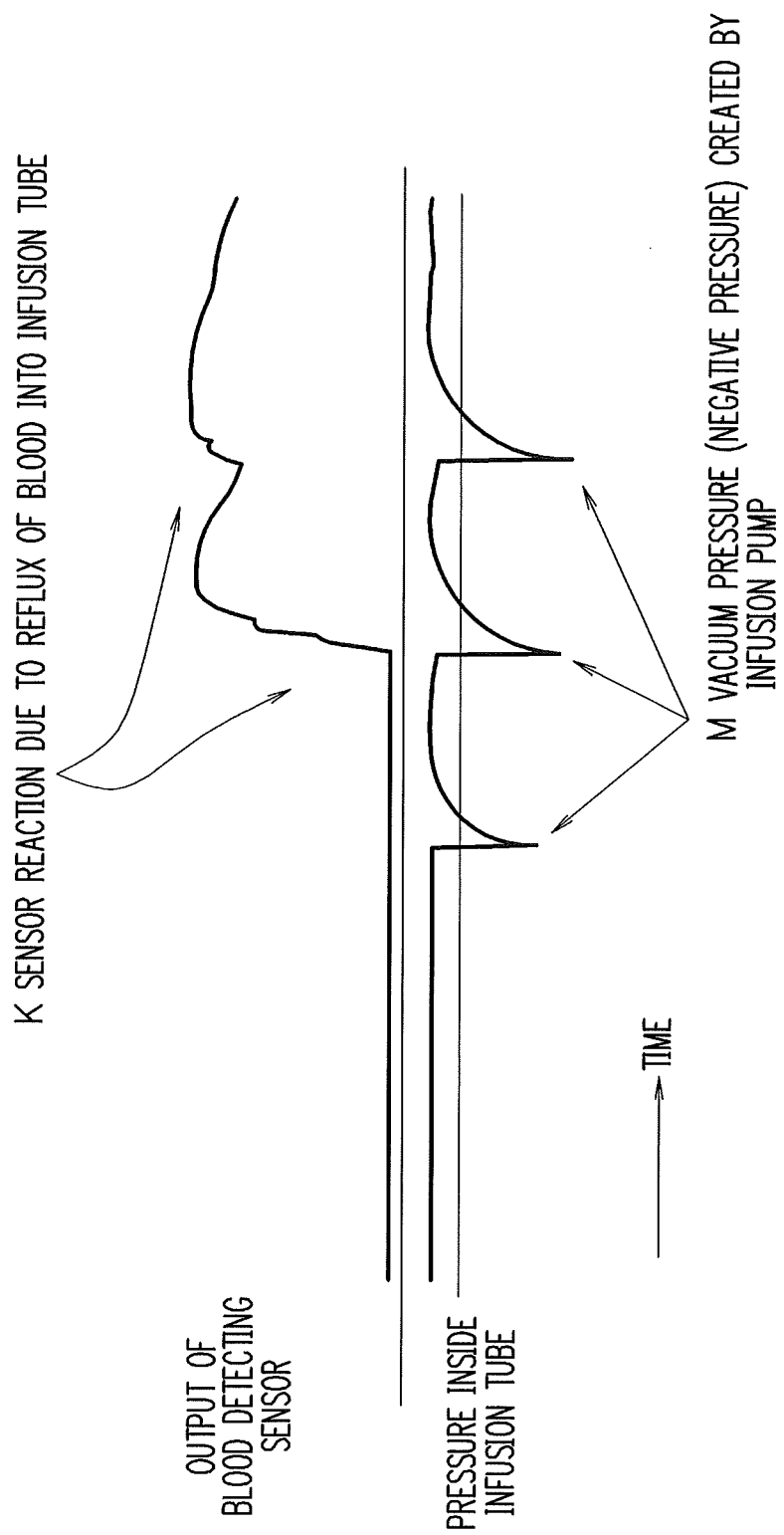
FIG. 8 is a diagram showing an operation of closing the infusion tube shown in FIG. 2 by an upstream closing unit causing pressure inside the infusion tube to drop at regular time intervals to generate vacuum pressure (negative pressure) M, and a sensor reaction K obtained by detecting a reflux of blood inside the infusion tube due to the blood being suctioned in accordance with the vacuum pressure M.

FIG. 8 shows an operation of closing the infusion tube 4 shown in FIG. 2 by the upstream closing unit 21 causing pressure inside the infusion tube 4 to drop at regular time intervals to generate vacuum pressure (negative pressure) M, and a sensor reaction K obtained by the blood detecting sensor 70 by detecting a reflux of blood inside the infusion tube 4 due to the blood being suctioned in accordance with the vacuum pressure M. In accordance with the vacuum pressure K, blood inside the blood vessel T reaches the infusion tube 4 and the blood detecting sensor 70 can detect the blood.

Figure 9:
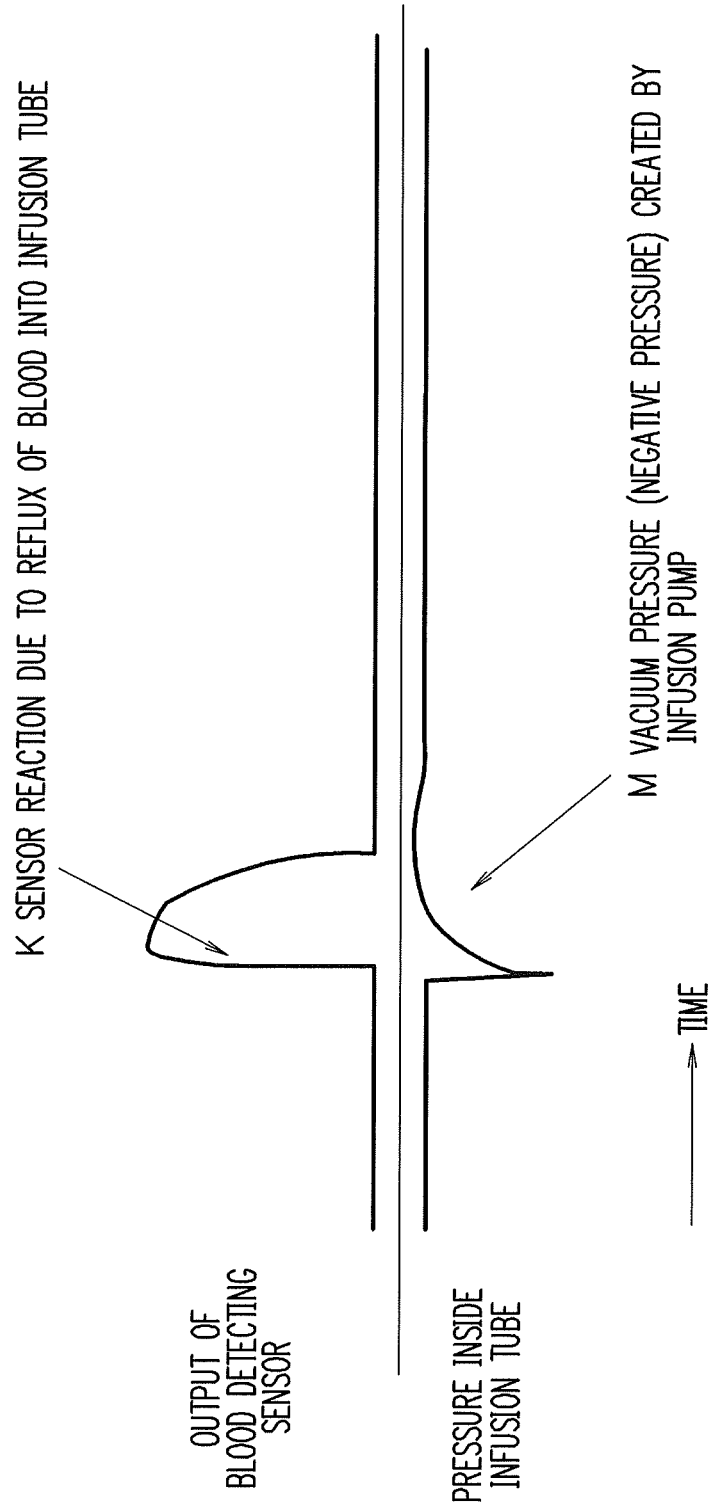
FIG. 9 is a diagram showing a drop of pressure inside the infusion tube causing vacuum pressure (negative pressure) M to be generated once, a sensor reaction K of a blood detecting sensor which is obtained by detecting a reflux of blood inside the infusion tube due to the blood being suctioned just once in accordance with the vacuum pressure M, and a subsequent restoration of a normal infusion state in which the blood does not reflux into the infusion tube.

FIG. 9 shows a drop of pressure inside the infusion tube 4 causing vacuum pressure (negative pressure) M to be generated once, a sensor reaction K of the blood detecting sensor 70 which is obtained by detecting a reflux of blood inside the infusion tube 4 due to the blood being suctioned once in accordance with the vacuum pressure M, and a subsequent restoration of a normal infusion state in which the blood does not reflux into the infusion tube 4. Accordingly, even if blood is refluxed from inside the blood vessel T to the inside of the infusion tube 4, there is no risk of the reflux of blood continuing afterwards and a normal infusion operation can be restored.

Figure 10:
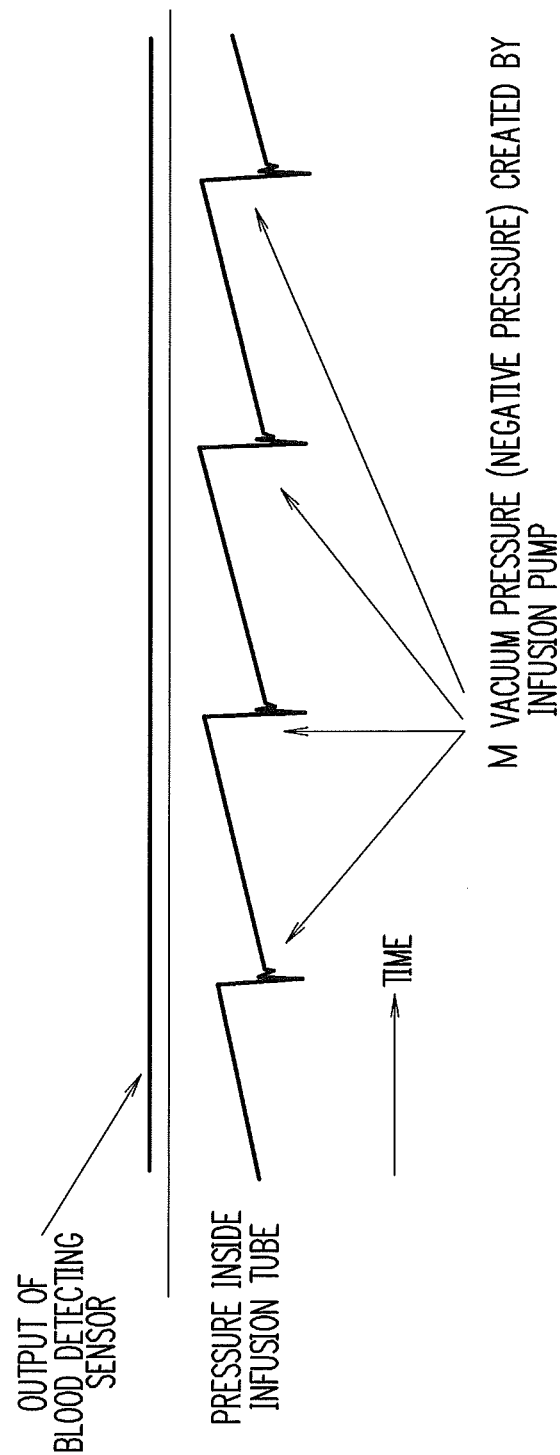
FIG. 10 is a diagram showing a situation where a catheter is dislodged from a blood vessel T and while pressure inside an infusion tube drops and vacuum pressure (negative pressure) M is generated periodically, a sensor reaction K does not occur because blood does not reflux into the infusion tube from inside the blood vessel.

FIG. 10 shows a situation where the tip opening 5A of the catheter 5 is dislodged from the blood vessel T and while pressure inside the infusion tube 4 drops and vacuum pressure (negative pressure) M is generated periodically, a sensor reaction K does not occur because blood does not reflux into the infusion tube 4 from inside the blood vessel T. As already described above, when there is no sensor reaction K even after negative pressure is generated a plurality of times, the control unit 22 shown in FIG. 2 judges that a state exists where the tip opening 5A of the catheter 5 has been dislodged from the blood vessel T and the fluid medicine is leaking out into surrounding subcutaneous tissue.

Next, other embodiments of the present invention will be described.

Figure 11:
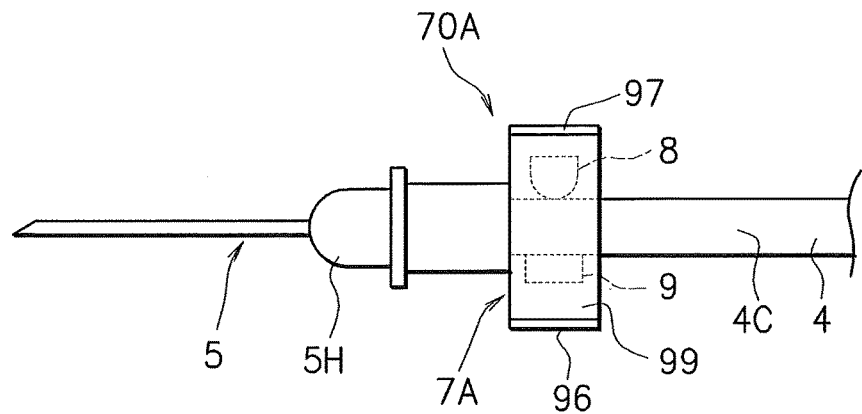
FIG. 11 is a diagram showing another embodiment of the present invention.

In the embodiment of the present invention shown in FIG. 11, a blood detecting sensor 70A is detachably mounted to a connecting portion 4C of an infusion tube 4 that is connected to a catheter 5. The blood detecting sensor 70A comprises a ring-like main body unit 7A, a light-emitting unit 8, and a light-receiving unit 9. The main body unit 7A is bisected into a divided portion 98 and a divided portion 99.

One end of the divided portion 98 and one end of the divided portion 99 are coupled by a hinge 97 so as to be openable and closable, and another end of the divided portion 98 and another end of the divided portion 99 are detachably fixed by a mounting tool 96 so as not to open. The light-emitting unit 8 is built into the divided portion 98 and the light-receiving unit 9 is built into the divided portion 99. Accordingly, the blood detecting sensor 70A can be detachably mounted to the connecting portion 4C of the infusion tube 4. In addition, the blood detecting sensor 70A can be added onto the connecting portion 4C of the infusion tube 4 or a peripheral portion thereof.

Figure 12:
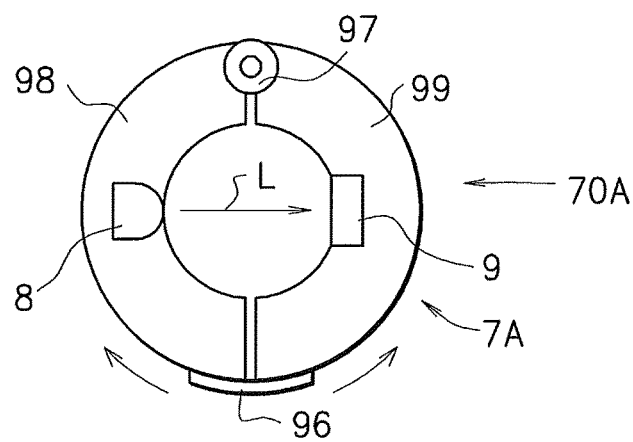
FIG. 12 is a diagram showing another embodiment of the present invention.
Figure 13:
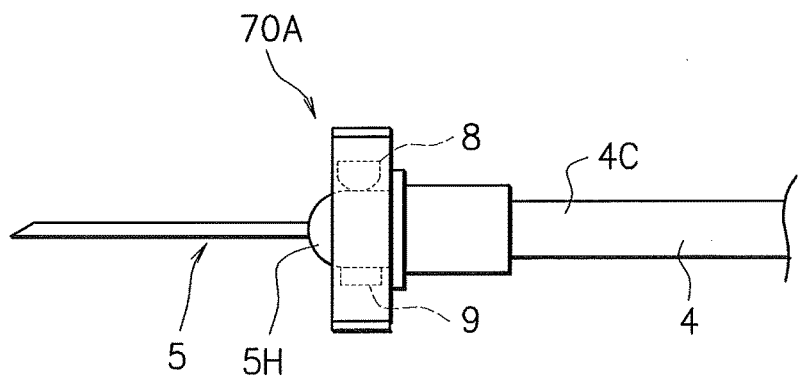
FIG. 13 is a diagram showing another embodiment of the present invention.

With an embodiment of the present invention shown in FIG. 13, the blood detecting sensor 70A shown in FIG. 12 is mounted to a hub 5H of a catheter 5. A ring-like main body unit 7A of the blood detecting sensor 70A shown in FIGS. 11 to 13 can be created from, for example, translucent plastic. Preferably, for example, a black light-blocking unit for blocking extraneous light may be formed in a peripheral portion of the main body unit 7A.

Figure 14:
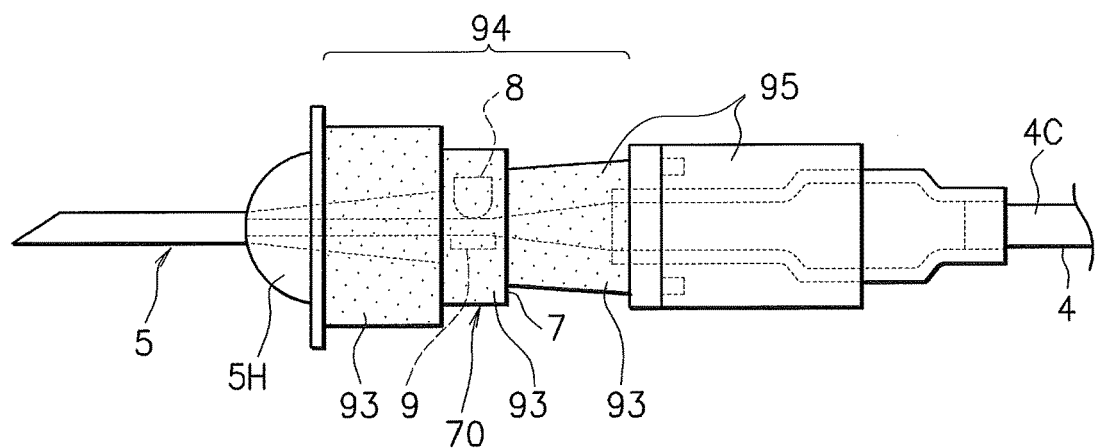
FIG. 14 is a diagram showing another embodiment of the present invention.

With an embodiment of the present invention shown in FIG. 14, a blood detecting sensor 7 is built into or fixed to a portion which is in a vicinity of a catheter 5 and which is near a connector 95 of a connecting portion 4C of an infusion tube 4. Preferably, for example, a black light-blocking unit 93 is formed on an outer circumferential surface of a region portion 94 including the blood detecting sensor 7. Accordingly, when light emitted by a light-emitting unit 8 is received by a light-receiving unit 9, the light-receiving unit 9 can be prevented from being influenced by ambient light.

Figure 15:
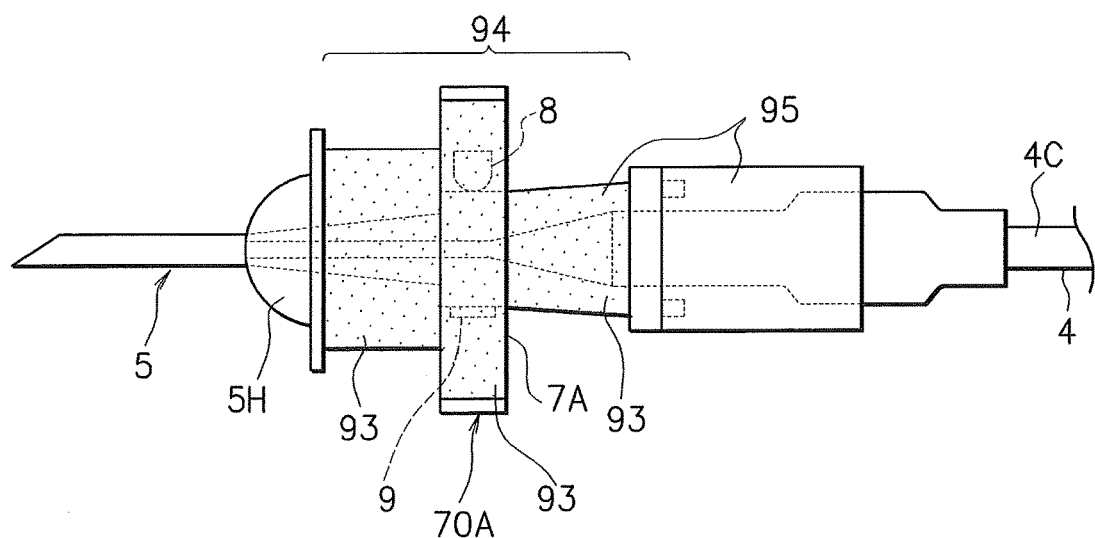
FIG. 15 is a diagram showing another embodiment of the present invention.

With an embodiment of the present invention shown in FIG. 15, a blood detecting sensor 70A such as that shown in FIG. 12 is detachably mounted to a portion which is in a vicinity of a catheter 5 and which is near a connector 95 of a connecting portion 4C of an infusion tube 4. Preferably, for example, a black light-blocking unit 93 is formed on an outer circumferential surface of a region portion 94 including the blood detecting sensor 7. Accordingly, when light emitted by a light-emitting unit 8 is received by a light-receiving unit 9, the light-receiving unit 9 can be prevented from being influenced by ambient light.

Yet other embodiments of the present invention will now be described with reference to FIGS. 16 to 19.

Figure 16:
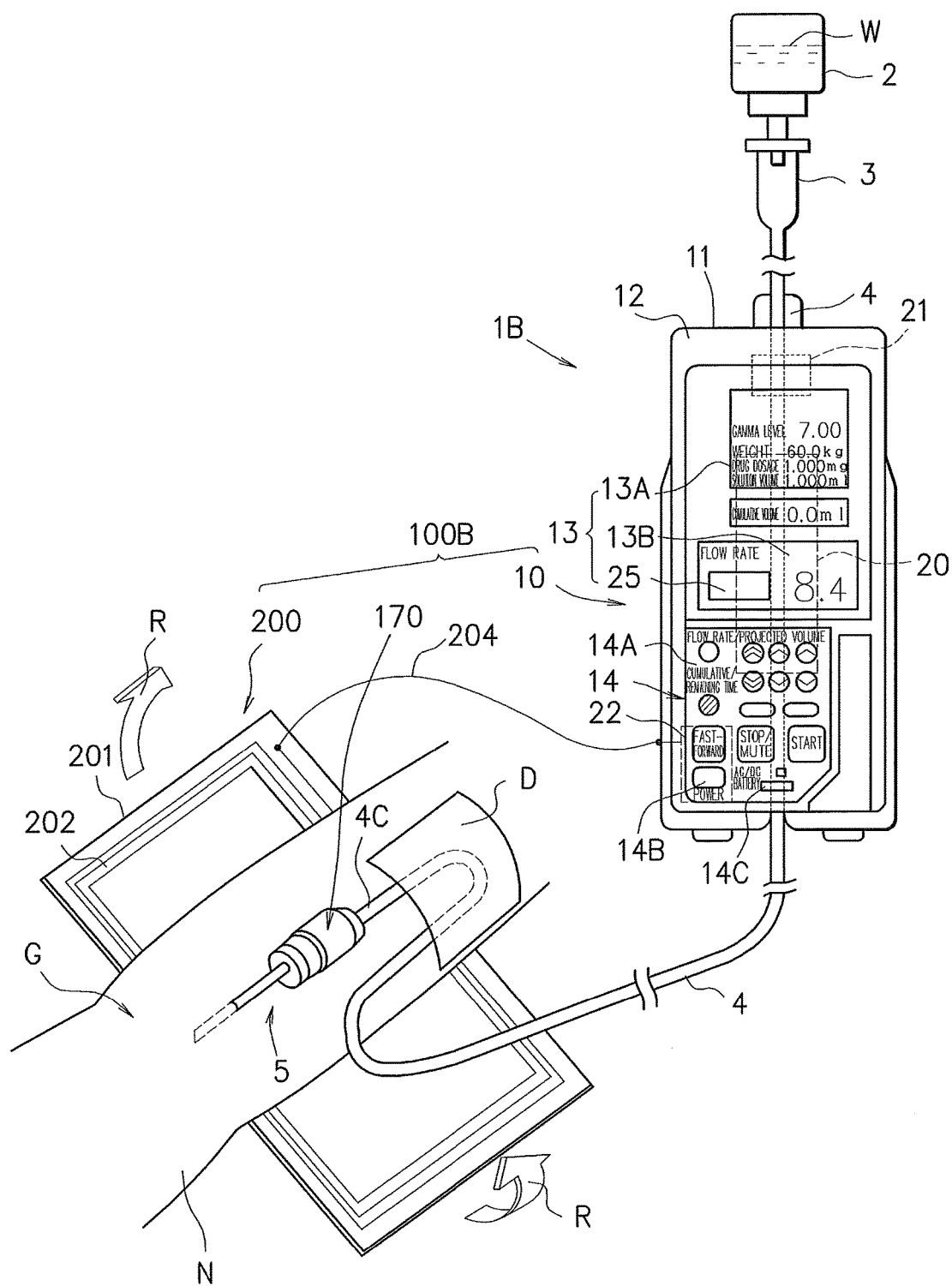
FIG. 16 is a diagram showing an infusion system including another embodiment of an extravasation detecting apparatus.

FIG. 16 shows an infusion system 1B including another embodiment of an extravasation detecting apparatus according to the present invention.

Since a fluid medicine bag 2, an instillation unit 3, an infusion pump 10, an infusion tube 4, and a catheter 5 of the infusion system 1B shown in FIG. 16 are substantially the same as the fluid medicine bag 2, the instillation unit 3, the infusion pump 10, the infusion tube 4, and the catheter 5 of the infusion system 1B shown in FIG. 1, descriptions of the latter will be used. However, the infusion system 1B shown in FIG. 16 differs in that the infusion system 1B comprises a blood detecting sensor 170 and a communication base unit 200 that is separate from the blood detecting sensor 170.

In addition, an extravasation detecting apparatus 100B is constituted by an upstream closing unit 21 of the infusion pump 10, a fluid delivery unit 20, the blood detecting sensor 170, and the communication base unit 200. The blood detecting sensor 170 and the communication base unit 200 constitute a so-called wireless tag (also referred to as an RF-ID or a contactless IC tag).

Figures 17A, 17B:
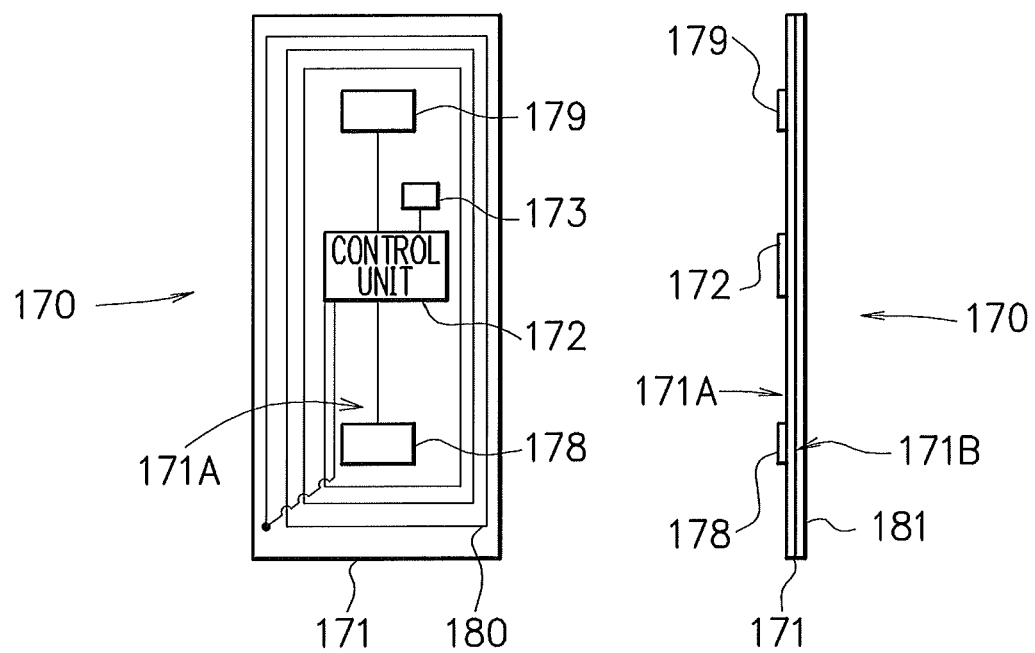
FIGS. 17A and 17B are diagrams showing a structural example of an expanded state of the blood detecting sensor shown in FIG. 16.
Figure 18:
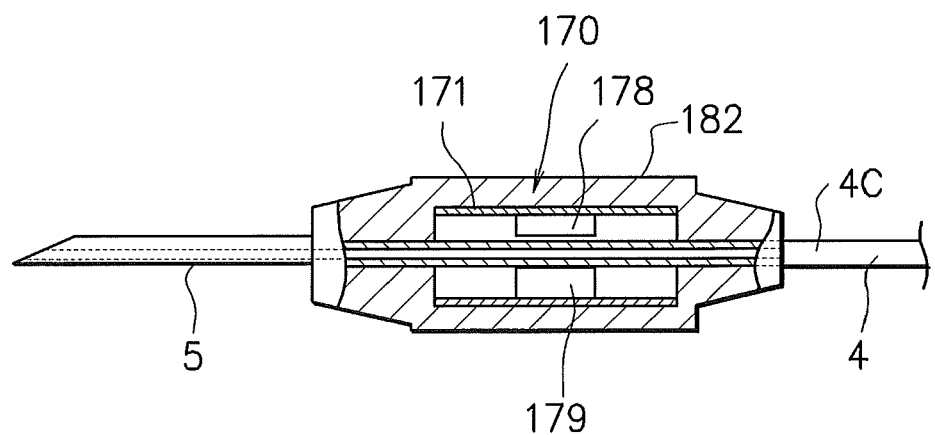
FIG. 18 is a side view including a partial cross section showing a state where the blood detecting sensor shown in FIG. 17 is fixed by winding the blood detecting sensor around a connector coupling unit of a catheter.

First, a structure of the blood detecting sensor 170 will be described. FIG. 17 shows a structural example of a state where the blood detecting sensor 170 shown in FIG. 16 has been expanded, wherein FIG. 17A is a front view showing a state where the blood detecting sensor 170 has been expanded and FIG. 17B is a side view of the blood detecting sensor 170. FIG. 18 is a side view including a partial cross section showing a state where the blood detecting sensor 170 shown in FIG. 17 is fixed by winding the blood detecting sensor 170 around a connecting portion 4C of the infusion tube 4.

As shown in FIG. 17, for example, the blood detecting sensor 170 comprises a wiring substrate 171 which has a rectangular shape and which is flexible and can be bent and rolled up, a control unit 172, a condenser 173, a light-emitting unit 178 and a light-receiving unit 179, and a first antenna unit 180 which provides both wireless communication and power feeding functions. For example, the light-emitting unit 178 is a light-emitting diode and the light-receiving unit 179 is a phototransistor. However, such an example is not restrictive. As the wiring substrate 171, for example, a film substrate, a flexible substrate, or the like which is flexible and can be bent and rolled up can be adopted.

The control unit 172 shown in FIG. 17 is electrically connected to the condenser 173, the light-emitting unit 178, the light-receiving unit 179, and the first antenna unit 180. The first antenna unit 180 is a loop coil-like antenna and is formed along four side portions on a side of a first surface 171A of the wiring substrate 171. The control unit 172, the condenser 173, the light-emitting unit 178, and the light-receiving unit 179 are arranged in a central vacant portion of the wiring substrate 171 which is formed by the first antenna unit 180.

The condenser 173 is a charging unit having a condenser capacity that enables charging of feeding power for causing the light-emitting unit 178 to perform a light-emitting operation at time intervals determined in advance such as every 15 minutes. The control unit 172 supplies the charge of the condenser 173 to the light-emitting unit 178 at the time intervals determined in advance to have the light-emitting unit 178 emit light. A light-blocking film 181 as a light-blocking unit is formed by, for example, screen printing on a side of a second surface 171B of the wiring substrate 171 in order to block extraneous light. Accordingly, when light emitted by the light-emitting unit 178 is received by the light-receiving unit 179, the light-receiving unit 179 can be prevented from being affected by ambient light.

With the blood detecting sensor 170 shown expanded in FIG. 17A, for example, by winding the blood detecting sensor 170 around the connecting portion 4C of the infusion tube 4 as shown in FIG. 18, the light-emitting unit 178 and the light-receiving unit 179 are arranged so as to face each other across the connecting portion 4C of the infusion tube 4. In addition, a periphery of the blood detecting sensor 170 wound in this manner is sealed by, for example, an insert-molded resin portion 182. Accordingly, the blood detecting sensor 170 can be fixed in a vicinity of the catheter 5 and the blood detecting sensor 170 and the catheter 5 can be integrated.

On the other hand, as shown in FIG. 16, the communication base unit 200 comprises a wiring substrate 201 and a second antenna unit 202 which provides both wireless communication and power feeding functions. The second antenna unit 202 is a loop coil-like antenna and is electrically connected to the control unit 22 of the infusion pump 10 by a wiring 204. For example, a film substrate, a flexible substrate, or the like that can be wound can be adopted as the wiring substrate 201.

Next, operation examples of the blood detecting sensor 170 and the communication base unit 200 above will be briefly described.

For example, by arranging the wiring substrate 201 shown in FIG. 16 so that the wiring substrate 201 is spread as-is around an arm N or, more preferably, by winding the wiring substrate 201 around the arm N in a direction of an arrow R, the blood detecting sensor 170 can be covered and a distance between the blood detecting sensor 170 and the communication base unit 200 can be reduced.

By feeding power to the second antenna unit 202 via the wiring 204, the control unit 22 of the infusion pump 10 shown in FIG. 16 creates electromagnetic induction that uses a magnetic field generated at the second antenna unit 202 of the communication base unit 200 and the first antenna unit 180 of the blood detecting sensor 170 shown in FIG. 17 as a transmission medium at, for example, a short wave band frequency of 13, 56 MHz between the second antenna unit 202 and the first antenna unit 180, and charges feeding power from the second antenna unit 202 to the condenser 173 via the first antenna unit 180.

Accordingly, due to the control unit 172 shown in FIG. 17 feeding power from the condenser 173 to the light-emitting unit 178, the light-emitting unit 178 shown in FIG. 18 performs pulsed emission at regular time intervals determined in advance to irradiate infrared rays to, for example, blood that is suctioned into the infusion tube 4, and the infrared rays are received by the light-receiving unit 179. The light-receiving unit 179 receives the infrared rays and generates and sends a light reception signal to the control unit 172. As a result, the control unit 172 can perform wireless communication from the first antenna unit 180 to the second antenna unit 202 of the communication base unit 200 and send the light reception signal from the light-receiving unit 179 to the control unit 22 of the infusion pump 10 via the wiring 204 shown in FIG. 16.

For example, the control unit 172 shown in FIG. 17 causes the light-emitting unit 178 to emit light four times in one hour, and a light reception signal from the light-receiving unit 179 is wirelessly transmitted from the first antenna unit 180 to the second antenna unit 202. Accordingly, the light reception signal is sent to the control unit 22 of the infusion pump 10 via the wiring 204, and the control unit 22 of the infusion pump 10 can detect at predetermined time intervals whether or not a tip of the catheter 5 is normally inserted into a blood vessel or, in other words, whether a fluid medicine is being administered into a blood vessel or the fluid medicine is leaking into surrounding subcutaneous tissue. If blood is suctioned into the infusion tube 4 or, in other words, if the tip opening 5A of the catheter 5 is inserted into a blood vessel, since a quantity of infrared rays is attenuated by blood, a judgment can be made that the catheter 5 is normally inserted into the blood vessel.

On the other hand, at times other than during light emission by the light-emitting unit 178, the control unit 22 of the infusion pump 10 charges feeding power from the second antenna unit 202 to the condenser 173 via the first antenna unit 180. Since the light-emitting unit 178 performs pulsed emission at predetermined time intervals, power consumption can be reduced.

Figures 19A, 19B:
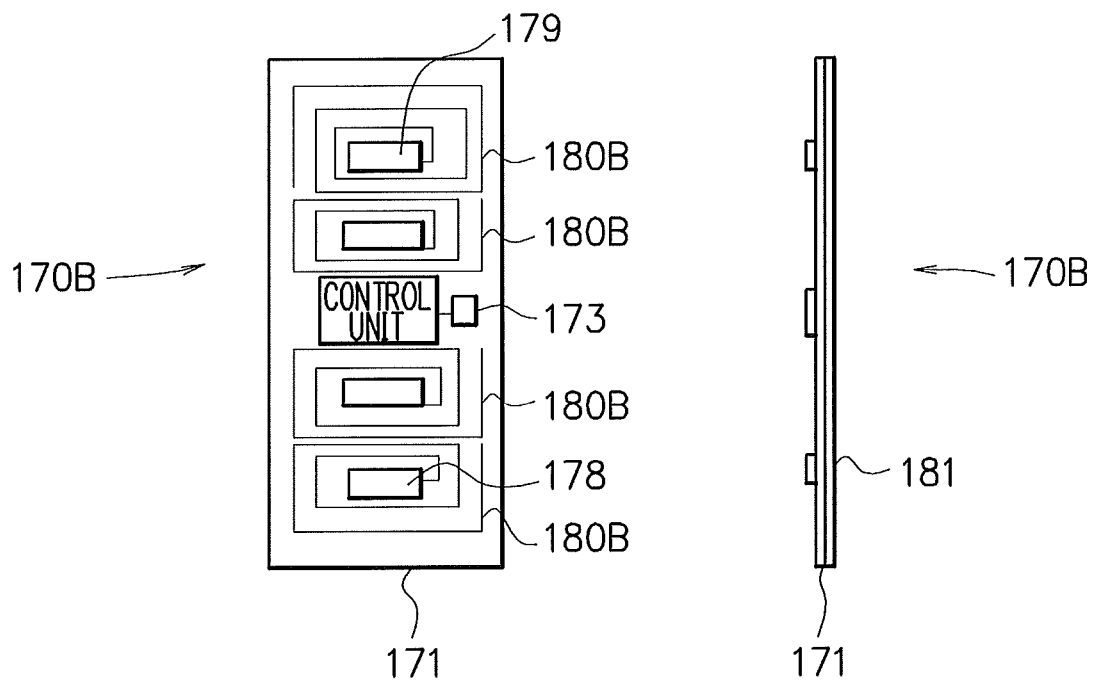
FIGS. 19A and 19B are diagrams showing another embodiment of a blood detecting sensor according to the present invention.

FIG. 19 shows another embodiment of a blood detecting sensor.

Besides a structure including one antenna unit, a blood detecting sensor 170B shown in FIG. 19 may be configured so that a plurality of antenna units such as four antenna units 180B are arranged in a longitudinal direction of a wiring substrate 171.

An extravasation detecting apparatus according to the present invention comprises: a fluid medicine containing unit which contains a fluid medicine and to which a catheter or an indwelling needle to be placed inside a blood vessel is connected by an infusion tube; a fluid delivery unit which supplies the fluid medicine by sequentially and repetitively pressing the infusion tube with a plurality of fingers; an upstream closing unit which is arranged at a portion of the infusion tube that is upstream of the fluid delivery unit and which closes the infusion tube; and a blood detecting sensor which places inside a blood vessel a tip opening of the catheter or the indwelling needle to be placed and which detects whether or not blood is suctioned into the infusion tube from inside the blood vessel upon closing of an upstream portion of the infusion tube by the upstream closing unit when the fluid delivery unit is running and negative pressure is generated in the infusion tube by a restoring force of the infusion tube, wherein when the blood detecting sensor detects that blood is being suctioned, a judgment is made that the tip opening of the catheter or the indwelling needle is still inside the blood vessel and an extravasation has not occurred, but when the blood detecting sensor detects that blood is not being suctioned, a judgment is made that the tip opening is outside the blood vessel and an extravasation has occurred.

Accordingly, by utilizing a phenomenon that blood is sucked into and returns to the infusion tube when the tip opening of the catheter or the indwelling needle is inside a blood vessel but blood does not return when the tip opening is outside of the blood vessel, dislodgment from the blood vessel and movement in subcutaneous tissue of the tip opening of the catheter or the indwelling needle can be directly detected. As a result, unlike conventional methods that detect a change caused by accumulation in subcutaneous tissue of a certain amount of a drug injected from a tip opening of a catheter or an indwelling needle having entered the subcutaneous tissue, extravasation can be detected at an early stage. In particular, in a case of infusion treatment using a drug such as anticancer drugs that is likely to cause inflammation, pain, or necrosis when injected into extravascular tissue such as subcutaneous tissue, leakage of a fluid medicine can be discovered at an early stage and damage to surrounding subcutaneous tissue can be kept to a minimum.

In addition, unlike conventional methods, a sensor that performs detection is arranged in an infusion tube. Therefore, since a sensor need not be arranged on a puncture site of a catheter or an indwelling needle or on a surrounding skin surface thereof, extravasation can be detected without obstructing observation of the puncture site and the surrounding skin surface by medical personnel.

In the extravasation detecting apparatus according to the present invention, preferably, the blood detecting sensor is provided in a vicinity of a needle-like member for detecting blood suctioned into an infusion tube.

Accordingly, a stroke length of the fingers of the fluid delivery unit can be kept short and detection can be made even when an amount of suctioned blood is small.

In the extravasation detecting apparatus according to the present invention, preferably, the blood detecting sensor comprises a light-emitting unit which irradiates light to the suctioned blood, a light-receiving unit which receives light having passed through the blood, and a main body unit which holds the light-emitting unit and the light-receiving unit, wherein a light-blocking unit for blocking extraneous light is provided in the main body unit.

Accordingly, an attenuation of irradiated light due to absorption and reflection of light by blood inside the infusion tube can be detected based on transmitted light whose light quantity is greater than that of reflected light, and detection can be performed with a better SN ratio than when using reflected light.

In addition, by providing the light-blocking unit, an erroneous judgment of a state where there is no return of blood which is made as a result of the light-receiving unit receiving extraneous light that cancels light reduction due to absorption by blood even when there is returning blood can be avoided and blood suctioned into the infusion tube can be reliably detected.

In the extravasation detecting apparatus according to the present invention, preferably, the light-emitting unit performs pulsed emission and synchronous detection at a frequency other than 50 Hz, 60 Hz, or a frequency that is a multiple thereof.

Accordingly, the light-receiving unit can perform detection accurately while avoiding a blinking frequency of a light source that is driven by a commercial AC power supply, and extraneous light such as a fluorescent light and light from a light bulb can be eliminated.

In the extravasation detecting apparatus according to the present invention, preferably, the blood detecting sensor includes a first antenna unit and a charging unit for feeding power to the light-emitting unit of the blood detecting sensor, the extravasation detecting apparatus further comprises a communication base unit that is separate from the blood detecting sensor, the communication base unit feeds power to the charging unit of the blood detecting sensor by electromagnetic induction between the first antenna unit of the blood detecting sensor, the blood detecting sensor transmits a signal based on a detection result of a presence or absence of the blood in the infusion tube from the first antenna unit of the blood detecting sensor to the base unit by wireless communication, and the communication base unit comprises a second antenna unit which notifies the received signal based on the detection result of the presence or absence of the blood in the infusion tube to an infusion pump which includes the fluid delivery unit.

Accordingly, the blood detecting sensor is capable of wirelessly sending and notifying electric energy necessary for operation and a detection signal of the presence or absence of blood to the infusion pump by wireless communication with the communication base unit that is separate from the blood detecting sensor. As a result, downsizing can be achieved since a power supply is no longer necessary, hygienic management of an indwelling site becomes easier since wiring is not required, and a so-called spaghetti syndrome caused by wiring can be reduced.

The respective embodiments of the present invention can be arbitrarily combined.

The present invention is not limited to the embodiments described above and various modifications can be adopted. Although the catheter 5 that is connected to the infusion tube 4 is used as a hollow member to be placed inside a blood vessel in the illustrated examples, an indwelling needle may be used instead of the catheter.

While the light-emitting unit preferably performs pulsed emission at a frequency other than 50 Hz, 60 Hz, or a frequency that is a multiple thereof, a pulsed emission frequency is sometimes not limited.

Hereinafter, another embodiment of the present invention will be described in detail with reference to the accompanying drawings and the like.

Moreover, although the embodiment described below is a preferred embodiment of the present invention and is therefore subject to various technically preferable limitations, it is to be understood that the scope of the present invention is not limited to these modes unless a description that particularly limits the present invention is given below.

Figure 20:
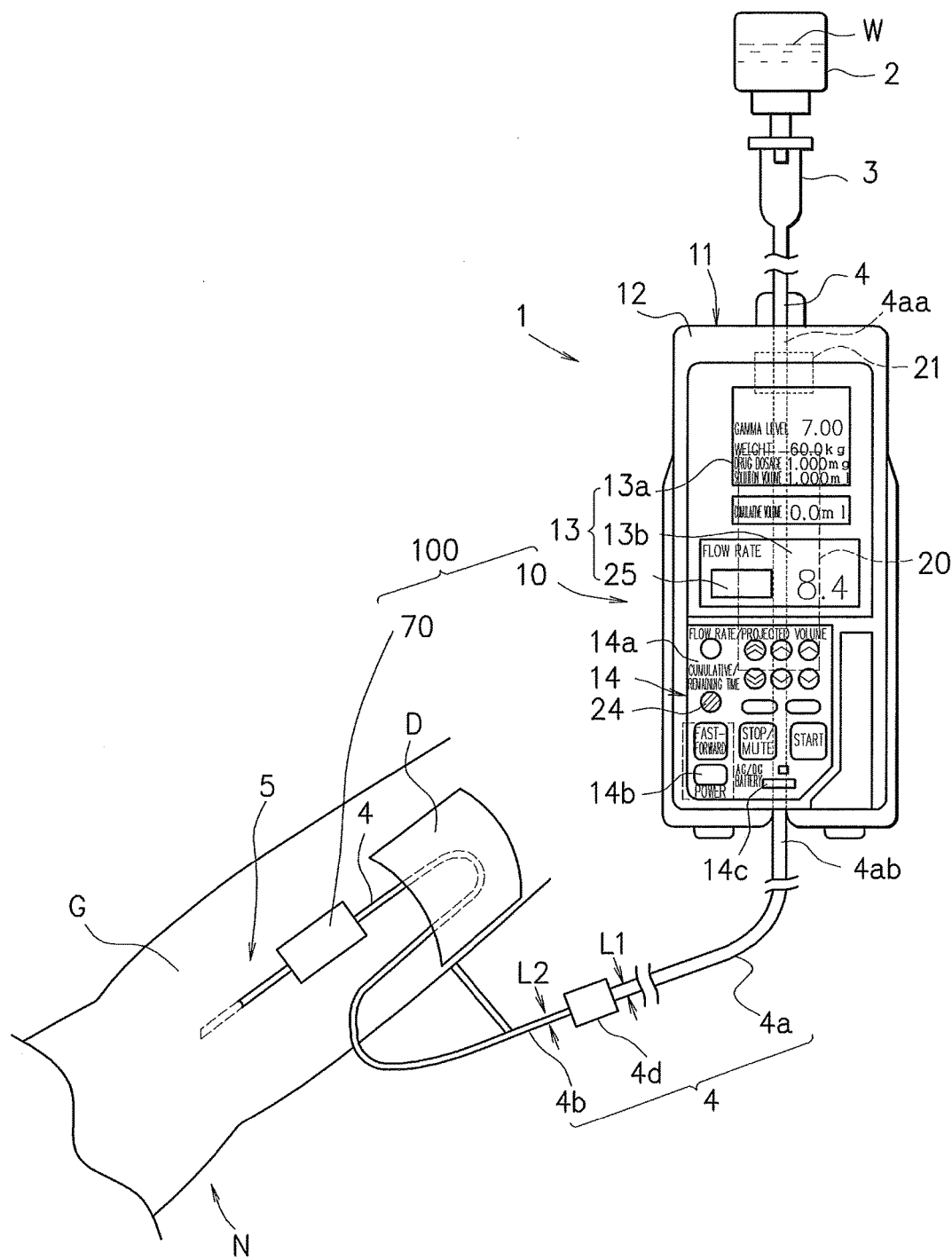
FIG. 20 is a schematic diagram showing an infusion system that is another embodiment of the present invention.
Figure 21:
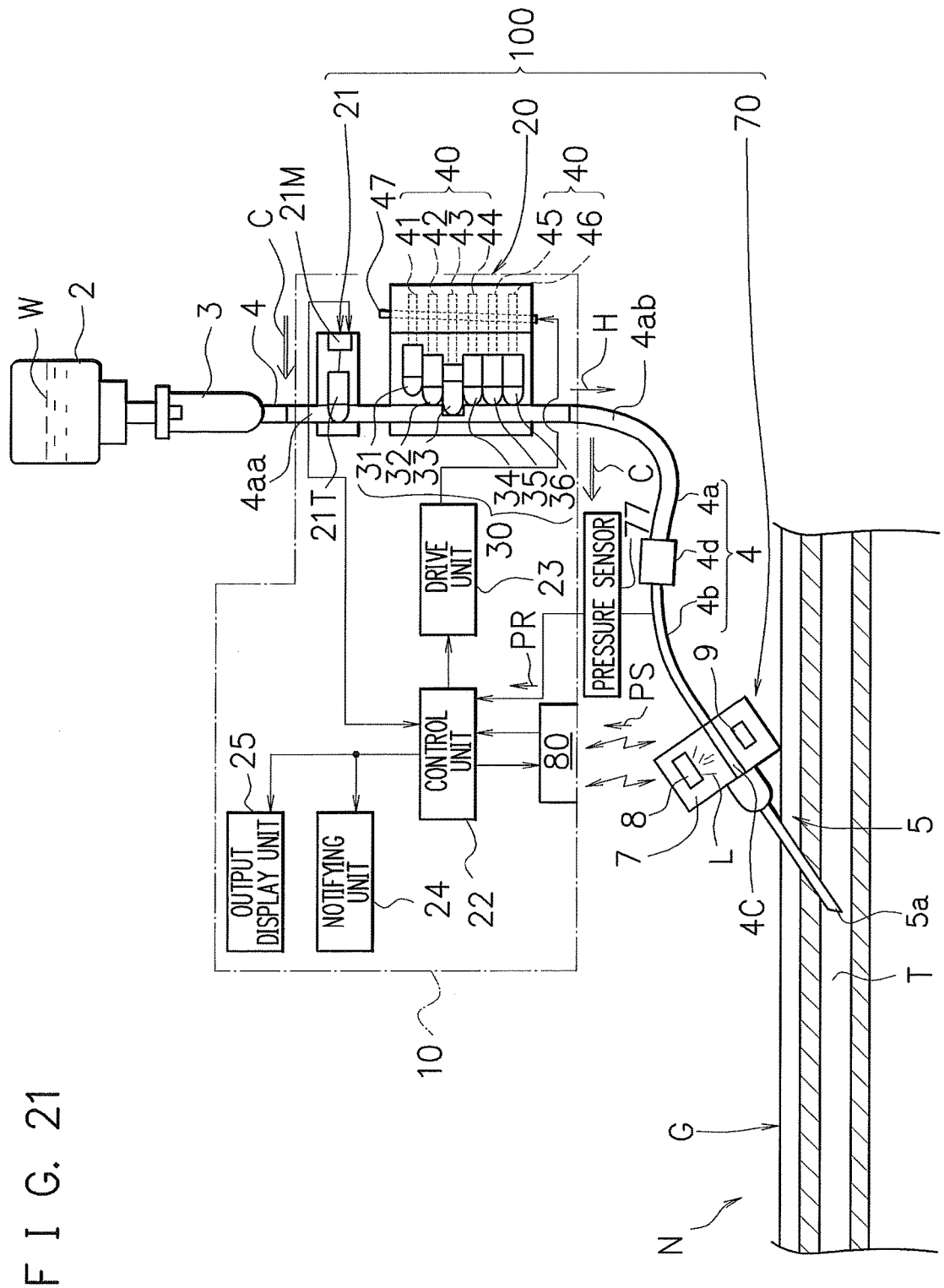
FIG. 21 is a schematic diagram showing a structural example of the infusion system shown in FIG. 1.

FIG. 20 is a schematic diagram showing an infusion system 1 that is another embodiment of the present invention, and FIG. 21 is a schematic diagram showing a structural example of the infusion system 1 shown in FIG. 20. Moreover, components similar to those of the embodiment described above are denoted by same reference numerals.

As shown in FIGS. 20 and 21, for example, the infusion system 1 comprises a fluid medicine bag 2 that is a fluid medicine (liquid) containing unit for containing a fluid medicine that is a liquid.

In addition, for example, the infusion system 1 comprises an instillation unit 3 for supplying the fluid medicine to an infusion tube 4 that is a liquid conveying unit, an infusion pump 10 that is a fluid delivery unit for controlling supply of the fluid medicine in the infusion tube 4, an indwelling vascular catheter or an indwelling needle 5 that is a solution supplying tool for actually supplying the fluid medicine into a blood vessel of a patient or the like.

For example, the indwelling vascular catheter 5 (hereinafter, simply referred to as a catheter) is configured so as to include a flexible tube and a junction (hub) which is provided at another end of the flexible tube and which connects the flexible tube with the infusion tube 4.

In addition, the indwelling needle is configured so as to include a metallic needle formed of stainless steel or the like, a flexible tube connected to the metallic needle, and a junction which is provided at a tip of the flexible tube and which connects the flexible tube with an infusion tube.

Furthermore, as shown in FIG. 20, the fluid medicine bag 2 internally contains a fluid medicine W. The fluid medicine bag 2 is detachably connected to the infusion tube 4 and the instillation unit 3 is integrally connected to the middle or one end of the infusion tube 4.

The infusion tube 4 is detachably passed through the infusion pump 10, and another end of the infusion tube 4 is detachably connected to the catheter (indwelling needle) 5.

The infusion tube 4 is also referred to as an infusion line.

As shown in FIGS. 20 and 21, for example, the infusion tube 4 comprises a normal diameter infusion tube 4a that is a normal diameter liquid conveying unit and a small diameter infusion tube 4b that is a small diameter liquid conveying unit. For example, the normal diameter infusion tube 4a and the small diameter infusion tube 4b can be attached and detached by an infusion tube connector 4d that is an attaching/detaching unit. For example, an inner diameter L1 (refer to FIG. 20) of the normal diameter infusion tube 4a is set to a diameter of 2 mm and the normal diameter infusion tube 4a is provided at a tip of the infusion tube 4 which has a normal diameter.

For example, an inner diameter L2 (refer to FIG. 20) of the small diameter infusion tube 4b is set to a diameter of 1.5 mm. The normal diameter infusion tube 4a is arranged on a side of the fluid medicine bag 2 and the infusion pump 10, and the small diameter infusion tube 4b is arranged on a side of the catheter 5. The normal diameter infusion tube 4a and the small diameter infusion tube 4b are connected to each other by the infusion tube connector 4d.

In other words, a configuration is realized in which the small diameter infusion tube 4b is attachable to and detachable from the normal diameter infusion tube 4a that is arranged on the side of the fluid medicine bag 2. As described above, since a user can readily mount the small diameter infusion tube 4b via the infusion tube connector 4d, an inner diameter of the infusion tube 4 can easily be reduced. Detailed operational effects of the normal diameter infusion tube 4a, the small diameter infusion tube 4b, and the like will be described later. Moreover, while the infusion tube 4 is configured so as to be divided into the normal diameter infusion tube 4a and the small diameter infusion tube 4b that are separate from one another in the present embodiment, the present invention is not limited thereto and a normal diameter portion and a small diameter portion of an infusion tube may be integrally formed.

The fluid medicine W inside the fluid medicine bag 2 shown in FIG. 20 enters the infusion tube 4. Due to a solution supplying operation by the infusion pump 10, the fluid medicine W inside the infusion tube 4 is supplied toward the catheter 5 at a flow rate (mL/h) set to the infusion pump 10.

For example, a vicinity of a connecting portion 4c of the infusion tube 4 on the side of the catheter 5 shown in FIG. 20 is attached to a surface of the skin G of an arm N of a human body by a piece of tape D.

As shown in FIG. 20, the infusion pump 10 comprises a main body 11 and a door 12. The door 12 is mounted to the main body 11 by a hinge and is openable and closable with respect to the main body 11.

A display unit 13 and an operating unit 14 are arranged on a surface of the door 12. For example, the display unit 13 is a liquid crystal display panel and comprises a display portion 13a which displays a so-called gamma level and weight and a flow rate display portion 13b which displays a flow rate of the fluid medicine W.

The operating unit 14 comprises a flow rate setting button 14a of the fluid medicine W, a power ON/OFF button 14b, a battery display portion 14c, and the like. A configuration is realized in which, by opening the door 12 from the main body 11, the infusion tube 4 can be passed into the main body 11 in a longitudinal direction.

FIG. 21 shows primary elements and the like arranged inside the infusion pump 10 shown in FIG. 20. For example, the infusion pump 10 comprises a fluid delivery unit 20, an upstream closing unit 21 that is a closing unit, a pump-side control unit 22 which is constituted by a RAM, a ROM, a microcomputer, and the like and which includes a judging unit and controls the entire apparatus, a drive unit 23, a notifying unit 24, and an output display unit 25.

The fluid delivery unit 20, the upstream closing unit 21, the pump-side control unit 22, and the drive unit 23 are arranged inside the main body 11 shown in FIG. 20.

For example, the notifying unit 24 is arranged in the operating unit 14 of the door 12 shown in FIG. 20. For example, the output display unit 25 is arranged in the display unit 13 of the door 12 shown in FIG. 20.

Returning to FIG. 21, the pump-side control unit 22 is electrically connected to the drive unit 23, the notifying unit 24, and the output display unit 26.

The notifying unit 24 may adopt at least one of a speaker which provides audio guidance, a buzzer which performs audio notifications, a lamp which performs optical notifications, and the like.

As shown in FIG. 21, the upstream closing unit 21 is arranged between the instillation unit 3 and the fluid delivery unit 20 and is provided in order to close an upstream portion 4*aa* of the normal diameter infusion tube 4*a* between the instillation unit 3 and the fluid delivery unit 20. Both the normal diameter infusion tube 4*a* and the small diameter infusion tube 4*b* are made of a thermoplastic resin which is flexible and highly restorative, and is translucent.

The upstream closing unit 21 comprises a pressing member 21T and an actuator 21M. The actuator 21M is electrically connected to the pump-side control unit 22. In response to an instruction issued by the pump-side control unit 22, the actuator 21M is capable of almost completely closing the upstream portion 4*aa* of the normal diameter infusion tube 4*a* by moving the pressing member 21T in a C direction toward the upstream portion 4*aa* of the normal diameter infusion tube 4*a*. In addition, since the upstream portion 4*aa* of the normal diameter infusion tube 4*a* can be opened by actuating the actuator 21M in reverse, the upstream portion 4*aa* can be restored to once again pass the fluid medicine W through. The C direction is a direction that is perpendicular to an axial direction of the normal diameter infusion tube 4*a*.

Next, a configuration of the fluid delivery unit 20 will be described with reference to FIG. 21.

As shown in FIG. 21, the drive unit 23 is, for example, an electric motor and is driven according to an instruction issued by the pump-side control unit 22. The fluid delivery unit 20 comprises the drive unit 23 and a pump mechanism unit 30. The pump unit 30 is arranged on a downstream side of the upstream closing unit 21 and comprises a plurality of fingers such as first to sixth fingers 31 to 36 and an operating cam unit 40. While an example having six fingers is illustrated, the number of fingers can be arbitrarily selected. The fluid delivery unit 20 employs a peristaltic system in which the normal diameter infusion tube 4*a* is sequentially pressed by the first to sixth fingers 31 to 36 to completely occlude the normal diameter infusion tube 4*a*. A solution supplying system which does not completely occlude the normal diameter infusion tube 4*a* may be employed instead.

The first to sixth fingers 31 to 36 shown in FIG. 21 are arranged lined up in an H direction from the upstream portion 4*aa* to a downstream portion 4*ab* along the normal diameter infusion tube 4*a*.

The operating cam unit 40 includes first to sixth cam surface portions 41 to 46. The first to sixth cam surface portions 41 to 46 are respectively arranged so as to correspond to the first to sixth fingers 31 to 36. The first to sixth cam surface portions 41 to 46 are fixed to a shaft portion 47 and have cam follower surfaces that differ from each other. Due to the drive unit 23 rotating the shaft portion 47 so that the first to sixth cam surface portions 41 to 46 respectively move in a C direction in a sequence of corresponding first to sixth fingers 31 to 36 according to an order to be described later, a position where the normal diameter infusion tube 4*a* is occluded can be varied.

A principle of supplying a solution by the fluid delivery unit 20 of the peristaltic infusion pump 10 described earlier with reference to FIGS. 22 and 23 and a principle of generating negative pressure by operating the fluid delivery unit 20 in a state where an upstream side is closed by the upstream closing unit 21 will now be described.

Figure 22:
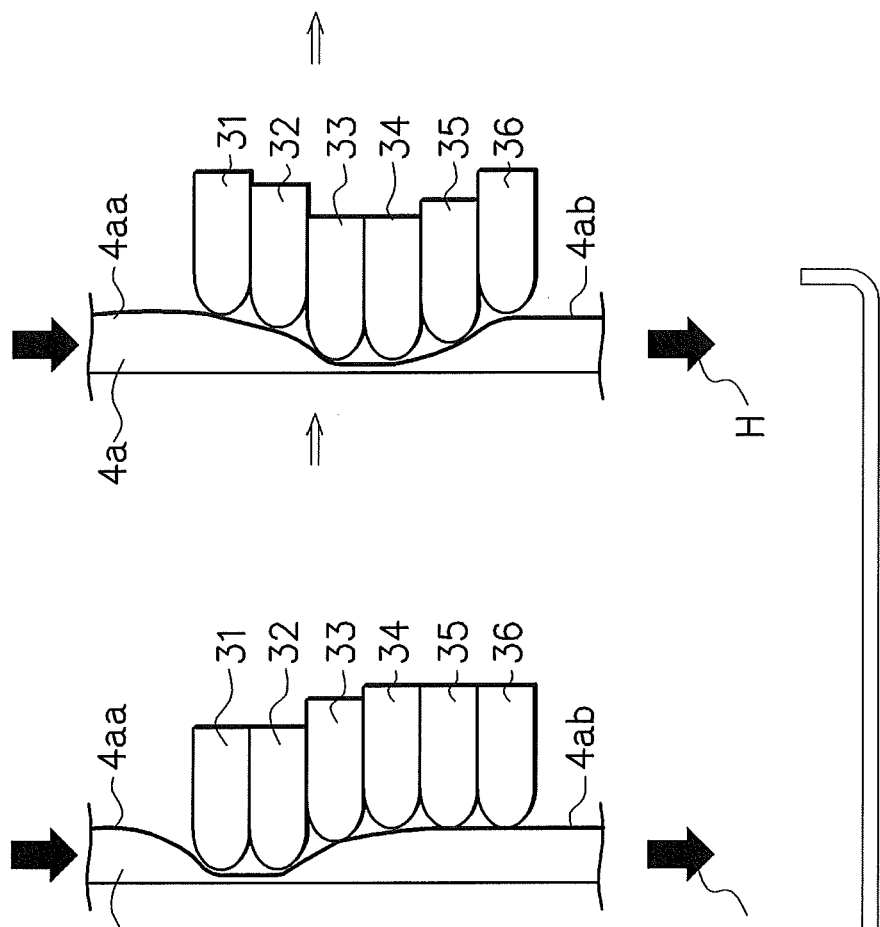
FIGS. 22A-22C are explanatory diagrams showing operation examples of supplying a fluid medicine inside an infusion tube by having first to sixth fingers sequentially press the infusion tube from an upstream portion to a downstream portion of the infusion tube.

FIG. 22 is an explanatory diagram showing an operation example of supplying a fluid medicine inside an infusion tube by having first to sixth fingers sequentially press the infusion tube 4*a* from the upstream portion 4*aa* to the downstream portion 4*ab* of the infusion tube 4*a*.

Figure 23:
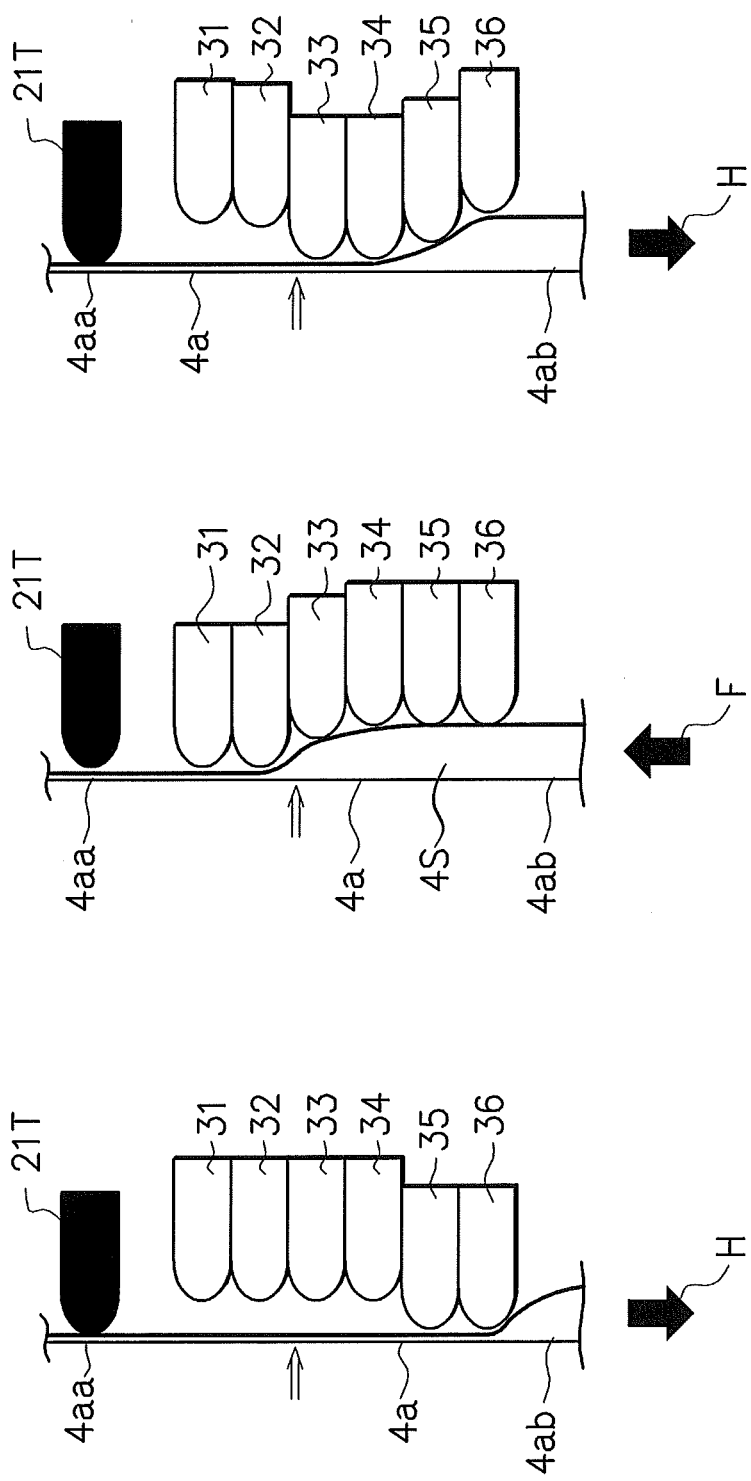
FIGS. 23A-23C are explanatory diagrams showing operation examples of performing suction of blood inside a blood vessel by generating negative pressure inside an infusion tube between an upstream portion and a downstream portion of the infusion tube.

FIG. 23 is an explanatory diagram showing an operation example of performing suction of blood inside a blood vessel by generating negative pressure inside the infusion tube 4*a* between the upstream portion and the downstream portion of the infusion tube 4*a*.

First, the principle of the fluid delivery unit 20 will be described with reference to FIG. 22. FIG. 22 shows an operation example of the first finger 31 and the like supplying a fluid medicine W inside the normal diameter infusion tube 4*a* at a set flow rate (mL/h) by having the first to sixth fingers 31 to 36 sequentially press and occlude the normal diameter infusion tube 4*a* from the upstream portion 4*aa* to the downstream portion 4*ab* of the normal diameter infusion tube 4*a* in the peristaltic infusion pump 10 described above.

A solution supplying operation will now be described with reference to FIG. 22.

FIGS. 22A, 22B, and 22C respectively show states of the first to sixth fingers 31 to 36 when a solution supplying operation by the fluid delivery unit 20 of the infusion pump 10 is being performed or stopped. The following description of the solution supplying operation will be centered on the state shown in FIG. 22A.

In FIG. 22A, a fluid medicine is injected into the normal diameter infusion tube 4*a* from the upstream portion 4*aa* in a state where the normal diameter infusion tube 4*a* is completely occluded by the fifth and sixth fingers 35 and 36. As the shaft portion 47 rotates, a cam causes the fifth finger 35 to return while leaving the sixth finger 36 as-is, and the first finger 31 is gradually pushed out. After regions P1 and P2 of the normal diameter infusion tube 4*a* enter an occluded state, the sixth finger 36 returns while the first finger 31 is left as-is, and the second finger 32 is gradually pushed out to create a state shown in FIG. 22B.

Subsequently, the first finger 31 returns while the second finger 32 is left as-is, and the third finger 33 is gradually pushed out. The normal diameter infusion tube 4*a* is occluded by the second and third fingers 32 and 33. At this point, the fluid medicine W is replenished from the upstream portion 4*aa* to a location that is restored due to the return of the first finger 31 while the fluid medicine W existing in a region that is occluded by the third finger 33 is pushed out into the downstream portion 4*ab*.

Subsequently, the second finger 32 returns while the third finger 33 is left as-is, and the fourth finger 34 is gradually pushed out. The normal diameter infusion tube 4*a* is occluded by the third and fourth fingers 33 and 34 to create a state shown in FIG. 22C.

Subsequently, the third finger 33 returns while the fourth finger 34 is left as-is, and the fifth finger 35 is gradually pushed out. The normal diameter infusion tube 4*a* is occluded by the fourth and fifth fingers 34 and 35.

Subsequently, the fourth finger 34 returns while the fifth finger 35 is left as-is, and the sixth finger 36 is gradually pushed out. The normal diameter infusion tube 4a is occluded by the fifth and sixth fingers 35 and 36 to create a state shown in FIG. 22A. The phases above are repeated.

With the above constituting a single cycle of the first finger 31 and the like, an internal volume from P1 to P2 shown in FIG. 22A of the normal diameter infusion tube 4a is supplied to the downstream portion 4ab.

The pump-side control unit 22 shown in FIG. 21 adjusts a flow rate of an infusion solution by changing the number of strokes per unit time with the internal volume described above corresponding to a single stroke.

Next, the principle of generating negative pressure by operating the fluid delivery unit 20 in a state where the upstream portion 4aa is closed by the upstream closing unit 21 will be described with reference to FIG. 23.

When the first finger 31 moves from the state shown in FIG. 22B with the upstream portion 4aa occluded and a state is reached where the normal diameter infusion tube 4a is completely occluded by the fifth and sixth fingers 35 and 36 as shown in FIG. 23A via the state shown in FIG. 22C, the fluid medicine is not injected into the normal diameter infusion tube 4a from the upstream portion 4aa and the normal diameter infusion tube 4a remains in a squashed state.

Subsequently, as the shaft portion 47 rotates, the cam causes the fifth finger 35 to return while leaving the sixth finger 36 as-is, and the first finger 31 is gradually pushed out. After regions P1 and P2 of the normal diameter infusion tube 4a enter an occluded state, the sixth finger 36 returns while the first finger 31 is left as-is, and the second finger 32 is gradually pushed out to create a state shown in FIG. 23B. When this state is reached, the squashed normal diameter infusion tube 4a is restored and the fluid medicine is rapidly suctioned by the downstream portion 4ab. Due to this phenomenon, the inside of the normal diameter infusion tube 4a at the downstream portion 4ab rapidly assumes negative pressure and blood is swiftly suctioned by the tip opening 5a of the catheter 5 shown in FIG. 21.

Subsequently, the first finger 31 returns while the second finger 32 is left as-is, and the third finger 33 is gradually pushed out. The normal diameter infusion tube 4a is occluded by the second and third fingers 32 and 33. At this point, while the fluid medicine W existing in a region occluded by the third finger 33 is pushed out into the downstream portion 4ab, the fluid medicine W is not replenished at a location that is restored by the return of the first finger 31 since the upstream portion 4ab is further closed and the location remains in a squashed state.

Subsequently, the second finger 32 returns while the third finger 33 is left as-is, and the fourth finger 34 is gradually pushed out.

The normal diameter infusion tube 4a is occluded by the third and fourth fingers 33 and 34 to create a state shown in FIG. 23C.

Subsequently, the third finger 33 returns while the fourth finger 34 is left as-is, and the fifth finger 35 is gradually pushed out. The normal diameter infusion tube 4a is occluded by the fourth and fifth fingers 34 and 35.

Subsequently, the fourth finger 34 returns while the fifth finger 35 is left as-is, and the sixth finger 36 is gradually pushed out. The normal diameter infusion tube 4a is occluded by the fifth and sixth fingers 35 and 36 to create a state shown in FIG. 23A and a volume suctioned into the normal diameter infusion tube 4a is restored. The phases above are repeated.

Blood that is swiftly suctioned is not returned into a blood vessel with a gentle pressing force of the fingers and remains, and when swiftly suctioned once again, the remaining blood is gradually transferred to the side of the infusion pump 10.

As described above, by repeating the operations shown in FIGS. 23A to 23C, periodic suction operations can be performed.

Next, an extravasation detecting apparatus 100 will be described with reference to FIG. 21.

For example, the extravasation detecting apparatus 100 comprises an infusion pump 10 including an upstream closing unit 21, a fluid delivery unit 20, and the like, and a blood detecting sensor 70 that is a blood detecting unit.

The extravasation detecting apparatus 100 is used to detect a dislodgment of the tip opening 5a of the catheter 5 from the blood vessel T instead of detecting an accumulation in subcutaneous tissue of a fluid medicine W leaking from the catheter 5.

In other words, by detecting that the tip opening 5a of the catheter 5 has been dislodged from the blood vessel T, a possibility that the fluid medicine W has leaked out into surrounding subcutaneous tissue of the skin G can be notified.

Figure 24:
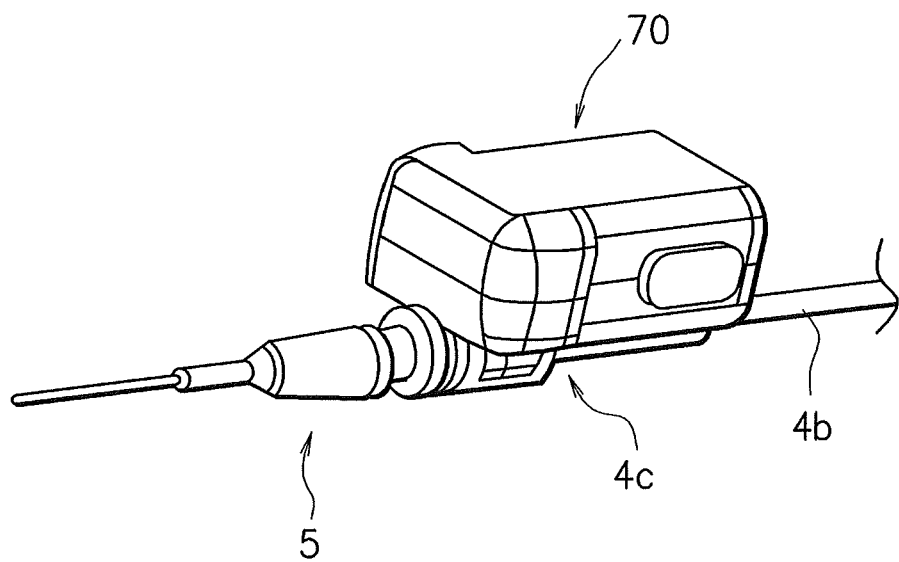
FIG. 24 is a schematic diagram showing a blood detecting sensor or the like arranged on a side of a small diameter infusion tube near a catheter.
Figure 25:
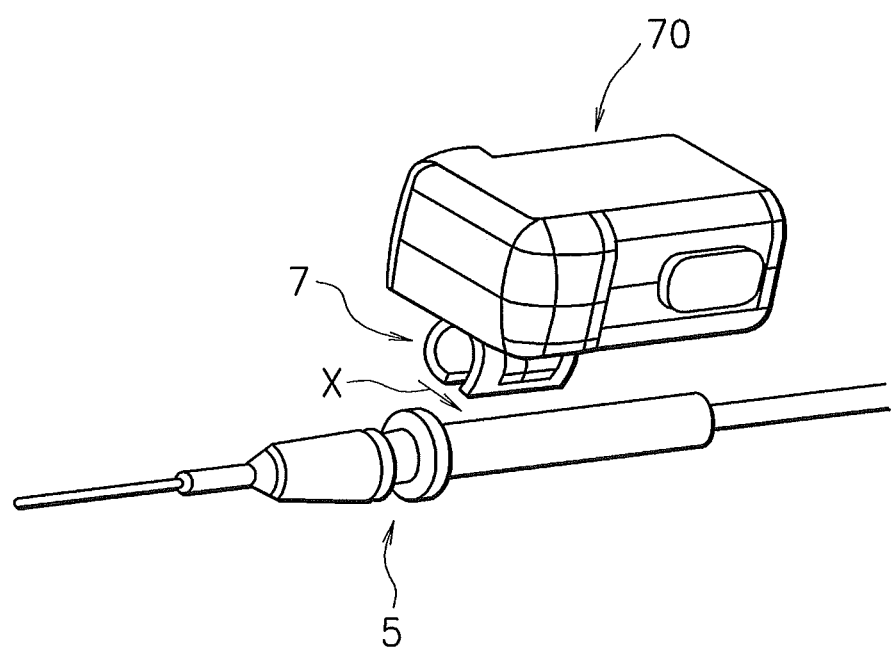
FIG. 25 is a schematic diagram showing a state where a blood detecting sensor has been detached from a catheter 5.

As shown in FIG. 21, for example, the blood detecting sensor 70 is arranged in a vicinity of the catheter 5. FIG. 24 is a schematic diagram showing the blood detecting sensor 70 and the like that is arranged in a vicinity of the catheter 5 on a side of the small diameter infusion tube 4b. As shown in FIG. 24, the blood detecting sensor 70 is fixed at a connecting portion 4c of the catheter 5 with the small diameter infusion tube 4b. In addition, as shown in FIG. 25, the blood detecting sensor 70 is configured so as to be separate from the connecting portion 4c of the catheter 5 and is detachable. FIG. 25 is a schematic diagram showing a state where the blood detecting sensor 70 has been detached from the catheter 5.

Since only a limited amount of blood can be suctioned at one time with the suction method described above, the blood detecting sensor 70 is desirably arranged in close proximity to the catheter 5. FIGS. 20 and 21 show a state where the tip opening 5a of the catheter 5 is inserted into a blood vessel (vein) T of the skin G of an arm N of a human body or, in other words, a state where infusion is normally performed.

As shown in FIGS. 21 and 25, for example, the blood detecting sensor 70 is configured so as to comprise a ring-like main body unit 7 that is to be mounted to the connecting portion 4c. In addition, a light-emitting unit 8 and a light-receiving unit 9 are formed in the main body unit 7 and are arranged so as to straddle the connecting portion 4c.

The light-emitting unit 8 preferably generates infrared rays. A configuration is realized in which, as indicated by the arrow X in FIG. 25, light L emitted by the light-emitting unit 8 passes through a portion of the small diameter infusion tube 4b through which a fluid medicine or blood passes and proceeds to the light-receiving unit 9, and is receivable by the light-receiving unit 9.

Therefore, the light-emitting unit 8 and the light-receiving unit 9 are arranged in the main body unit 7 so as to oppose each other across the connecting portion 4c and the small diameter infusion tube 4b on the outside of the small diameter infusion tube 4b.

For example, a light-emitting diode, a laser diode, and the like can be used as the light-emitting unit 8. For example, a photodiode, a phototransistor, and the like can be used as the light-receiving unit 9.

In response to an instruction issued by the pump-side control unit 22, the light-emitting unit 8 preferably performs pulsed emission at a frequency other than 50 Hz, 60 Hz, or a frequency that is a multiple thereof and the light-receiving unit 9 detects a variable component of received light quantity synchronized with the frequency of the light emitted by the light-emitting unit 8.

Accordingly, the light-receiving unit can perform detection accurately while avoiding a blinking frequency of a light source that is driven by a commercial AC power supply, and extraneous light such as a fluorescent light and light from a light bulb can be eliminated.

The light-emitting unit 8 generates infrared rays in response to a signal from the pump-side control unit 22. The light-receiving unit 9 converts the received light L into an electric signal and sends the electric signal to the pump-side control unit 22 as a light reception signal PS. A configuration is realized in which, based on a reduction of received light quantity of the light L (infrared rays) at the light-receiving unit 9 caused by the infrared rays being blocked by blood passing through the small diameter infusion tube 4b, a passage of blood through the small diameter infusion tube 4c and the connecting portion 4c can be detected.

In addition, the blood detecting sensor 70 is configured so as to wirelessly communicate with the infusion pump 10 shown in FIG. 21.

Therefore, a user of the infusion system 1 need not arrange signal lines and handling by the user becomes easier. In addition, since there is no need for signal lines, hygienic management of the catheter 5 and the like becomes easier and a so-called spaghetti syndrome where signal lines become intertwined can be reduced.

Figure 26:
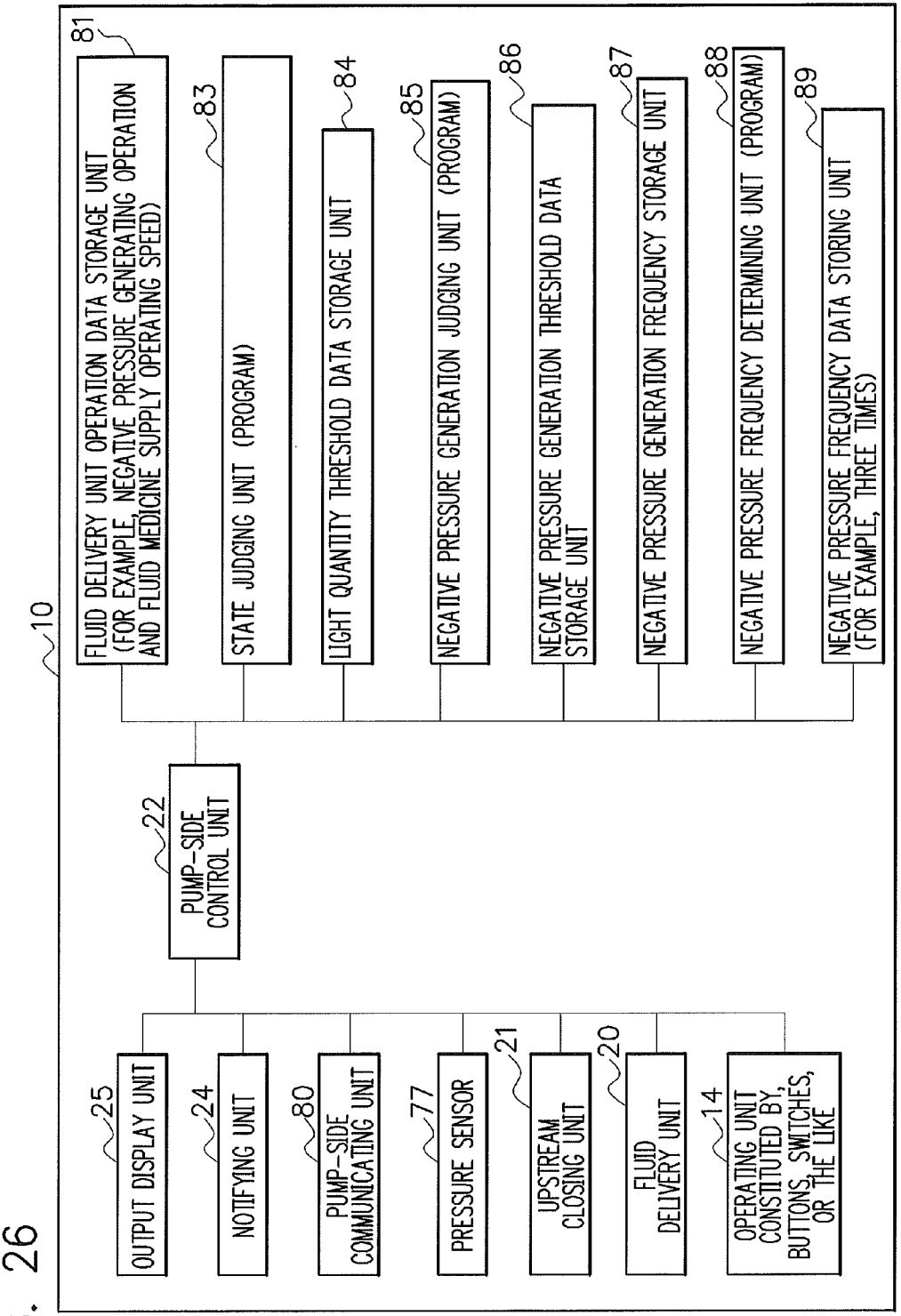
FIG. 26 is a schematic block diagram showing primary components of an infusion pump shown in FIGS. 20 and 21.
Figure 27:
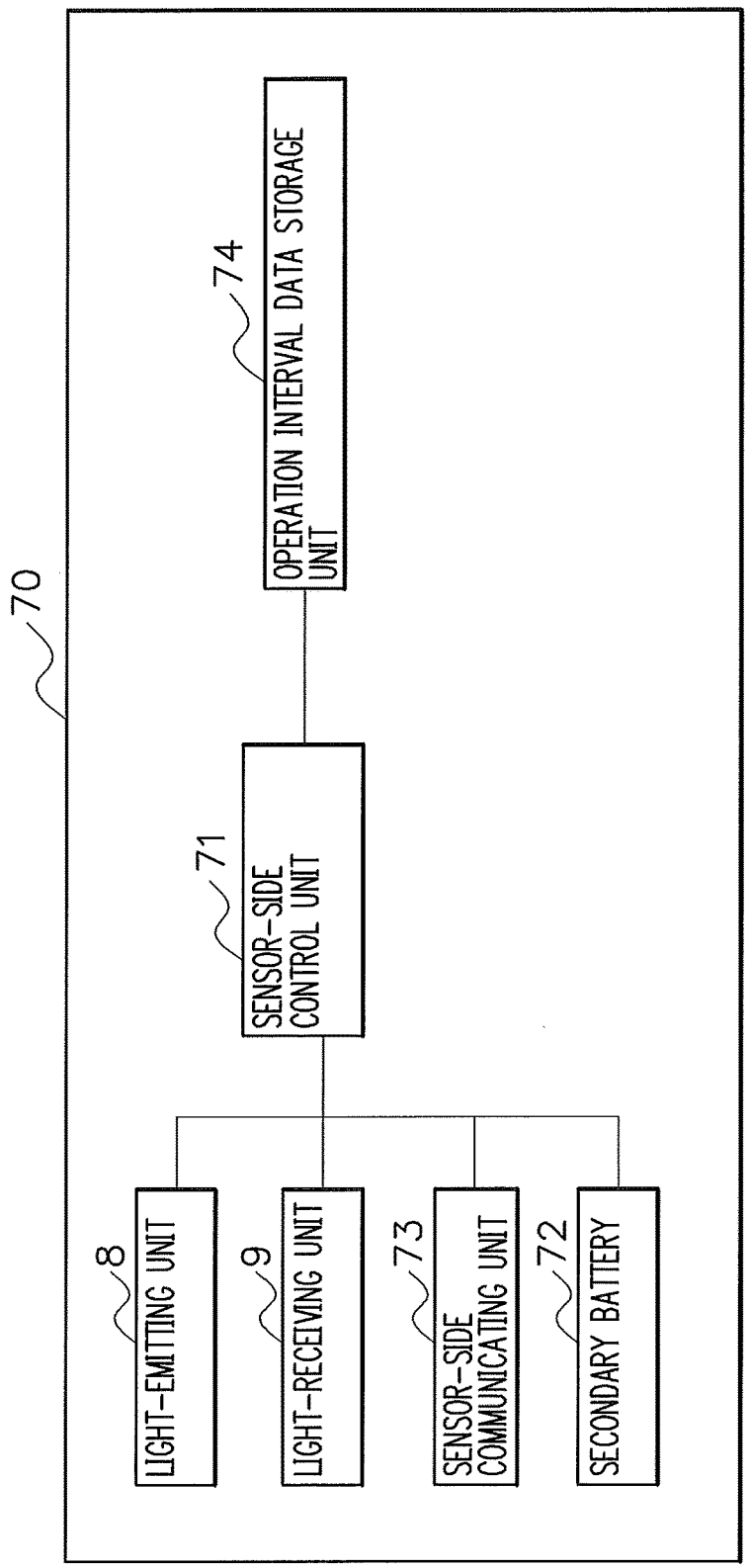

FIG. 26 is a schematic block diagram showing primary components of the infusion pump 10 shown in FIGS. 20 and 21, and FIG. 27 is a schematic block diagram showing primary components of the blood detecting sensor 70 shown in FIGS. 20, 21, and the like.

As shown in FIG. 26, the infusion pump 10 comprises a pump-side control unit 22, and the output display unit 25, the notifying unit 24, the upstream closing unit 21, the fluid delivery unit 20, the operating unit 14 constituted by buttons and/or switches, and the like described earlier are connected to the pump-side control unit 22.

In addition, a pump-side communicating unit 80 for the infusion pump 10 to communicate with the blood detecting sensor 70 and the like, a pressure sensor 77 for detecting that the small diameter infusion tube 4b or the like is under negative pressure, and the like are also connected to the pump-side control unit 22.

Moreover, while the infusion pump 10 comprises various programs, storage units, and the like which are also controlled by the pump-side control unit 22 as shown in FIG. 26, a description thereof will be given later.

Furthermore, as shown in FIG. 27, a sensor-side control unit 71 is provided, and the light-emitting unit 8, the light-receiving unit 9, and the like described earlier are connected to the sensor-side control unit 71.

In addition, a secondary battery 72 and a sensor-side communicating unit 73 for the blood detecting sensor 70 to communicate with the infusion pump 10 are connected to the sensor-side control unit 71. The storage unit shown in FIG. 8 will be described later.

Figure 28:
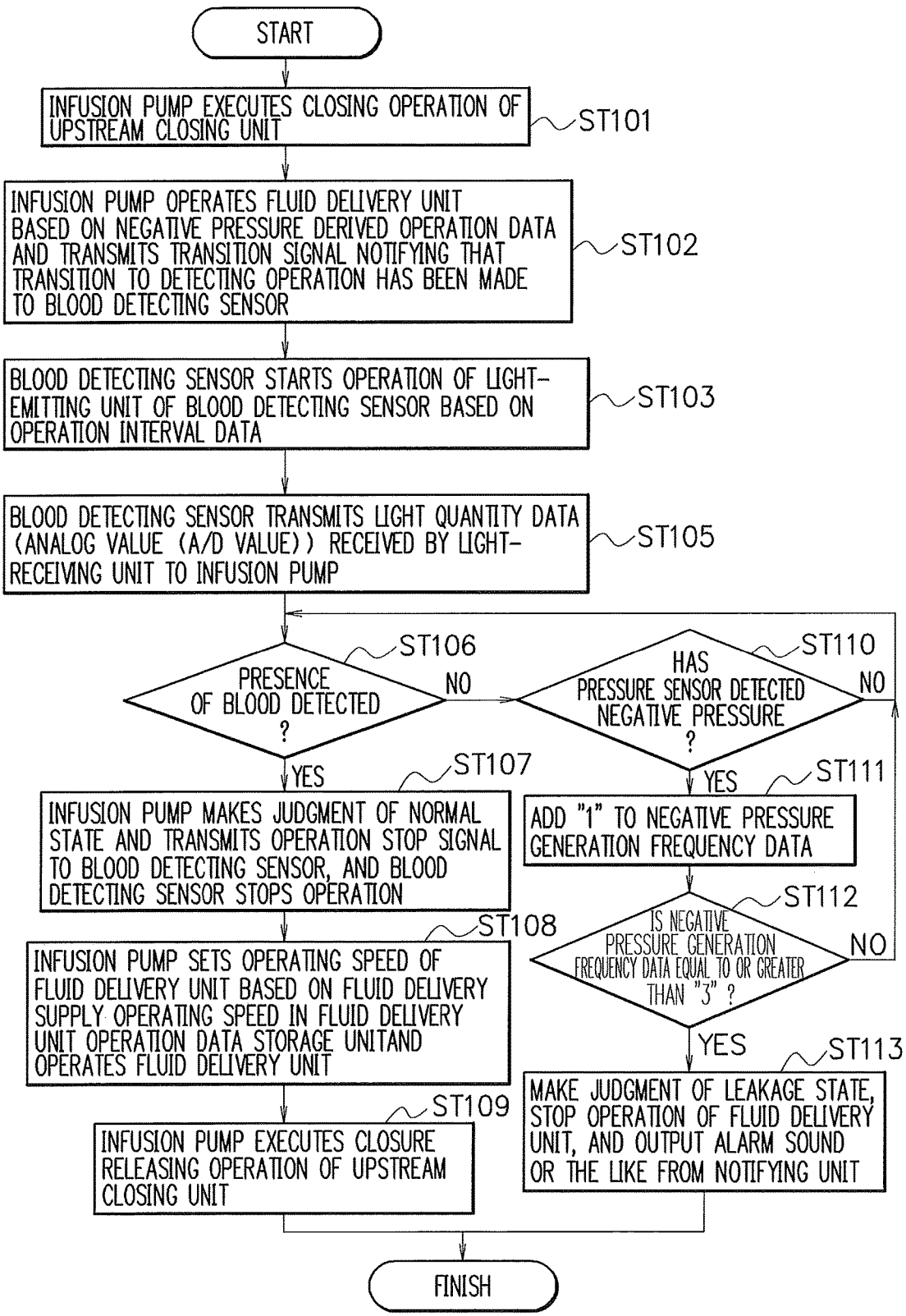
FIG. 28 is a schematic flow chart showing a primary operation example of an infusion system according to the present embodiment.

FIG. 28 is a schematic flow chart showing a primary operation example of the infusion system 1 according to the present embodiment. Hereinafter, the flow chart shown in FIG. 28 will be described together with the components shown in FIGS. 26, 27, and the like.

With the infusion system 1 according to the present embodiment, first, the main body unit 7 of the blood detecting sensor 70 is mounted to the catheter 5 or the like as shown in FIG. 24.

In this state, when a switch of the infusion pump 10 shown in FIG. 20 has been turned on and the infusion pump 10 is performing a supplying operation of a fluid medicine, whether or not the tip opening 5a of the catheter 5 is dislodged from a blood vessel T of an arm N of a patient or the like shown in FIG. 20 is checked at predetermined intervals.

In other words, during an infusion operation of the fluid medicine W shown in FIG. 21, an infusion operation mode is switched to an extravasation confirmation mode to start detection of blood. Hereinafter, the extravasation confirmation mode will be described in detail.

First, as described in step ST101 (hereinafter, a step will be denoted as ST) in FIG. 28, the infusion pump 10 shown in FIG. 20 and the like is operated and a closing operation of the upstream closing unit 21 is executed. In other words, the actuator 21M of the upstream closing unit 21 shown in FIG. 21 moves and causes the pressing member 21T to move in a direction of an arrow C to squash the upstream portion 4aa of the normal diameter infusion tube 4a, and closes the upstream portion 4aa as shown in FIG. 23.

Next, the extravasation confirmation mode proceeds to ST102. In ST102, the infusion pump 10 operates the fluid delivery unit 20 based on negative pressure generating operation data and transmits a transition signal notifying that a transition has been made to a detecting operation (extravasation confirmation mode) to the blood detecting sensor 70 shown in FIG. 20 and the like.

Specifically, for example, based on negative pressure generating operation data inside a fluid delivery unit operation data storage unit 81 shown in FIG. 26, an operating speed of the first to sixth fingers 31 to 36 shown in FIG. 21 of the fluid delivery unit 20 is changed so that negative pressure is generated at regular intervals in the infusion tube 4.

In other words, the first to sixth fingers 31 to 36 cause blood inside the blood vessel T to be suctioned from the tip opening 5a of the catheter 5 by generating negative pressure in the infusion tube 4 (the normal diameter infusion tube 4a and the small diameter infusion tube 4b) through the negative pressure generating operation shown in FIGS. 23A to 23C.

Moreover, an operating speed of the first to sixth fingers 31 to 36 for normal solution supplying is determined based on a fluid velocity of an infusion solution.

In addition, the infusion pump 10 wirelessly transmits the "transition signal" described above to the blood detecting sensor 70 via the pump-side communicating unit 80 shown in FIG. 26.

Next, the extravasation confirmation mode proceeds to ST103. In ST103, when the sensor-side communicating unit 73 shown in FIG. 27 of the blood detecting sensor 70 diagnoses the "transition signal" from the infusion pump 10, the blood detecting sensor 70 starts a light-emitting operation by the light-emitting unit 8 based on data inside an operation interval data storage unit 74 shown in FIG. 27.

In other words, in the blood detecting sensor 70, the light-emitting unit 8 emits infrared rays in a direction of an arrow X in FIG. 25 at regular intervals, and the light L is transmitted through the small diameter infusion tube 4b in FIG. 24 and received by the light-receiving unit 9.

Next, the extravasation confirmation mode proceeds to ST105. In ST105, for example, the blood detecting sensor 70 transmits light quantity data (an analog value (A/D value)) that is blood basic information received by the light-receiving unit 9 to the infusion pump 10 via the sensor-side communicating unit 73 as a light reception signal PS.

In ST106, the infusion pump 10 having received the light quantity data judges whether or not blood has returned into the small diameter infusion tube 4b of the connecting portion 4c based on the light quantity data received in ST105.

Specifically, a state judging unit (program) 83 of the infusion pump 10 shown in FIG. 26 operates and compares the light quantity data in the light reception signal PS with light quantity threshold data in a light quantity threshold data storage unit 84 to judge whether or not light quantity has decreased by a certain amount or more.

In other words, when blood has returned into the small diameter infusion tube 4b, the light quantity received by the light-receiving unit 9 decreases accordingly. A judgment on whether or not blood has returned is made by storing, in advance, data of the decreased light quantity and the like as light quantity threshold data.

A decrease in the light quantity by a threshold or more in ST6 means that blood has returned or, in other words, the tip opening 5a of the catheter 5 is normally placed inside the blood vessel T.

When the infusion pump 10 judges in ST106 that the light quantity has decreased by the threshold or more, the extravasation confirmation mode proceeds to ST107 in which the infusion pump 10 judges that the catheter 5 is normally placed and transmits an "operation stop signal" to the blood detecting sensor 70.

As a result, the blood detecting sensor 70 stops a light-emitting operation by the light-emitting unit 8 and the like.

Next, the extravasation confirmation mode proceeds to ST108. In ST108, the infusion pump 10 sets an operating speed of the fluid delivery unit 20 based on a fluid medicine supply operating speed in a fluid delivery unit operation data storage unit 81 shown in FIG. 26 and causes the fluid delivery unit 20 to operate at the set operating speed.

Subsequently, in ST109, the infusion pump 10 moves the pressing member 21T of the upstream closing unit 21 in a direction opposite to an arrow C. As a result, negative pressure inside the infusion tube 4 (the normal diameter infusion tube 4a and the small diameter infusion tube 4b) is released and blood suctioned during negative pressure is once again returned into the blood vessel T together with the fluid medicine W.

However, at this point, a phenomenon where blood fails to return may occur depending on a magnitude of a diameter of the infusion tube 4 and an orientation of the catheter 5. Generally, a specific gravity of blood is greater than that of a fluid medicine. Therefore, when a tip of the indwelling catheter 5 faces a direction opposite to a force of gravity or, in other words, when the fluid medicine and blood must proceed through a tube against a direction of a force of gravity, blood that had refluxed due to a suctioning operation is more likely to move in the direction of a force of gravity inside the infusion tube 4. As a result, a phenomenon occurs where the blood further refluxes in the infusion tube 4 or the blood continues to remain in the tube due to a balance in viscosity with respect to the fluid medicine.

Figure 29A:
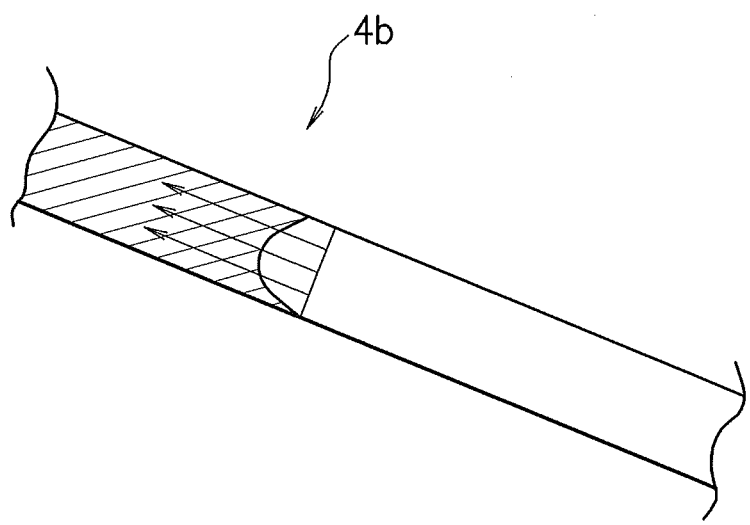
Figure 29B:
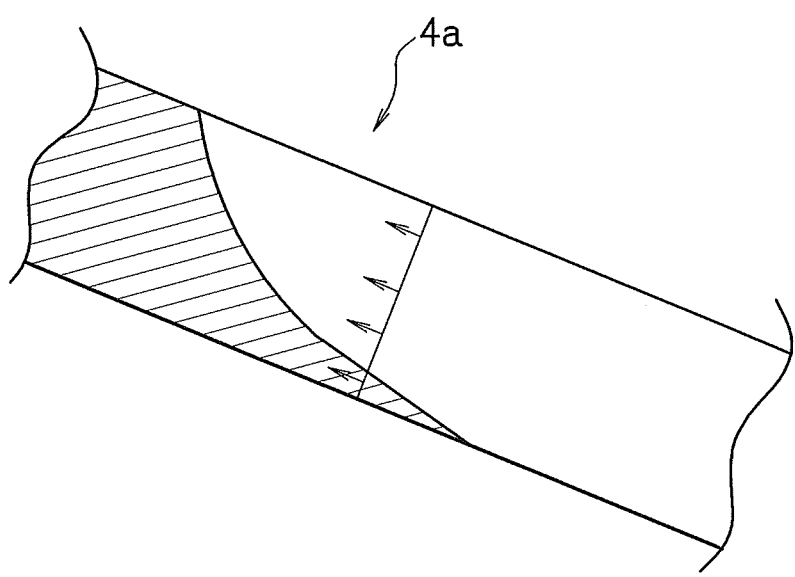

FIG. 29 is an explanatory schematic diagram showing a relationship between a diameter of the infusion tube 4 and return of blood when the tip of the catheter 5 faces a direction opposite to a force of gravity, wherein FIG. 29A shows a case of a small diameter infusion tube 4b with an inner diameter of 1.5 mm and FIG. 29B shows a case of a normal diameter infusion tube 4a with an inner diameter of 2 mm.

When the inner diameter is equal to or greater than a certain magnitude (for example, 2 mm) as shown in FIG. 29B, due to the fluid medicine and blood replacing each other in the infusion tube 4 in a state where the tip of the catheter faces a direction that is opposite to the force of gravity, phenomena occur such as blood not returning to the blood vessel and continuing to remain in the infusion tube 4 and blood further refluxing in the infusion tube. When blood continues to remain in the infusion tube, even if a reflux of blood due to negative pressure does not occur upon performing a next detecting operation, the blood sensor 70 ends up detecting blood based on remaining blood that had refluxed upon a previous detecting operation and may result in an erroneous judgment.

In consideration thereof, in the present embodiment, the inner diameter is set small to around 1.5 mm as shown in FIG. 29A. As a result, since a movement speed of the fluid medicine and blood passing through the small diameter tube 4b increases and a viscous force of the fluid medicine also increases, blood is now able to overcome the force of gravity and return into the blood vessel. Therefore, a configuration is realized in which blood in the infusion tube 4 can be completely returned to the blood vessel before the next negative pressure operation and a risk of an occurrence of such erroneous judgments can be forestalled.

However, since reducing the inner diameter increases pressure loss, when the tip of the catheter 5 faces a direction that is opposite to the force of gravity, blood no longer refluxes to the infusion tube 4 even if negative pressure is applied. Therefore, a judgment on whether the tip opening 5a of the catheter is placed inside the blood vessel T can no longer be made.

FIG. 30 is a graph showing a relationship among an inner diameter of the infusion tube 4, blood suction (during negative pressure), and return. In this graph, data regarding blood suction is data indicating whether or not suction occurs when the tip opening 5a of the catheter 5 faces downward, and the return of suctioned blood is represented by data indicating whether or not a return occurs when the tip opening 5a of the catheter 5 faces upward or, in other words, when the fluid medicine and the suctioned blood advance against the force of gravity.

Therefore, the inner diameter of the small diameter infusion tube 4b is preferably set to 1.1 mm to 2.1 mm and to, for example, 1.5 mm in the most preferred present embodiment.

On the other hand, if the infusion pump 10 is unable to detect the presence of blood in ST106, the extravasation confirmation mode proceeds to ST110 shown in FIG. 28.

In ST110, the pressure sensor 77 shown in FIG. 21 and the like judges whether or not pressure inside the small diameter infusion tube 4b and the like has been detected.

Specifically, a negative pressure generation judging unit (program) 85 shown in FIG. 26 operates and compares pressure data of the pressure sensor 77 with data in a negative pressure generation threshold data storage unit 86 shown in FIG. 26 to judge whether or not the pressure of the pressure sensor 77 is negative pressure.

When it is judged in ST110 that negative pressure has been generated, the extravasation confirmation mode proceeds to ST111. In ST111, "1" is added to negative pressure generation frequency data in a negative pressure generation frequency storage unit 87 shown in FIG. 26 and is registered thereto.

Next, the extravasation confirmation mode proceeds to ST112. In ST112, a judgment is made on whether or not the negative pressure generation frequency data shown in FIG. 26 is equal to or greater than a certain value.

Specifically, a negative pressure frequency judging unit (program) 88 shown in FIG. 26 operates and refers to negative pressure generation frequency data stored in the negative pressure generation frequency storage unit 87, and makes a judgment by comparing the data with a predetermined value such as "3" in a negative pressure frequency data storing unit 89 shown in FIG. 26.

In ST112, when the infusion pump 10 judges that the negative pressure frequency of the small diameter infusion tube 4b and the like is equal to or greater than "3", the extravasation confirmation mode proceeds to ST113.

In ST113, in consideration of the fact that the presence of blood has not been detected in ST106 despite a negative pressure state in the small diameter infusion tube 4b and the like being repeated a predetermined number of time or, in other words, three times, a judgment is made that suction of blood from the catheter 5 or the like is not taking place or, in other words, the tip opening 5a of the catheter 5 is dislodged from the blood vessel T.

In other words, a judgment of a state where the fluid medicine W is leaking is made, the operation of the fluid delivery unit 20 is stopped, and an alarm sound or the like is outputted from the notifying unit 24 shown in FIG. 20 and the like to notify a user or the like.

Specifically, for example, the notifying unit 24 is used to issue a notification to a patient or medical personnel by means of a buzzer sound, an audio announcement, or a warning light and to generate an alarm, and an alarm display is provided on the output display unit 25.

Accordingly, by detecting that the tip opening 5a of the catheter 5 is dislodged from a blood vessel, medical personnel can visually or audibly confirm a possibility that leakage of the fluid medicine has occurred.

As described above, according to the present embodiment, a dislodgment of a catheter 5 or the like from a blood vessel T can be reliably detected at an early stage.

In particular, in a case where a liquid such as an anticancer drug is injected into extravascular tissue such as subcutaneous tissue or in a case of infusion treatment using a liquid such as a drug that is more likely to cause inflammation, pain, necrosis, or the like and a leakage of a fluid medicine or the like occurs, the configuration described above enables a dislodgment of a catheter 5 or the like to be detected at an early stage. Therefore, damage to surrounding subcutaneous tissue can be kept to a minimum.

In addition, unlike conventional methods, a blood detecting sensor 70 that performs detection is arranged in correspondence with a small diameter infusion tube 4b or the like.

Therefore, since the blood detecting sensor 70 need not be arranged on a puncture site of the catheter 5 into a human body or on a surrounding skin surface thereof, a dislodgment of the catheter 5 or the like can be detected without obstructing observation of the puncture site and the surrounding skin surface by medical personnel.

Furthermore, in the present embodiment, an inner diameter of the small diameter infusion tube 4b is set smaller than an inner diameter of a normal diameter infusion tube 4a to, for example, 1.5 mm. As shown, since a diameter of the small diameter infusion tube 4b on a near side to the blood vessel T is set to, for example, 1.5 mm, a configuration is realized in which blood having refluxed from the blood vessel T to a side of a liquid conveying unit is likely to be returned into the blood vessel even when negative pressure in an infusion tube 4 or the like is released.

Therefore, when detection of dislodgment of a solution supplying tool such as the catheter 5 or the like is performed a plurality of times during administration of an infusion solution, an erroneous judgment due to blood remaining in the liquid conveying unit from a previous detection can be avoided.

Moreover, while the infusion pump 10 is configured so as to judge a presence or absence of blood in the small diameter infusion tube 4b based on light quantity data from the blood detecting sensor 70 in the present embodiment, this configuration is not restrictive and the judgment of the presence or absence of blood may instead be performed by the blood detecting sensor 70.

In addition, while the present embodiment is configured so that an absence of blood is judged based on negative pressure frequency when a presence of blood cannot be detected in ST110 and the like, this configuration is not restrictive and the same judgment may be made based on a lapse of a certain amount of time.

Furthermore, while negative pressure is detected using a pressure sensor 77 in the present embodiment, a negative pressure state may alternatively be judged without using the pressure sensor 77 by estimating a timing where negative pressure is generated in the infusion tube 4 based on operating states of the first to sixth fingers 31 to 36 of the fluid delivery unit 20. For example, according to the description given above, negative pressure is generated when the sixth finger 36 returns while the first finger 31 is left as-is, and the second finger 32 is gradually pushed out to create a state shown in FIG. 23B. Accordingly, a negative pressure state may be judged once the state shown in FIG. 23B is created.

FIGS. 31 and 32 are schematic flowcharts showing another modification of the present embodiment.

Since many components and steps of an operation example of the present modification are similar to those of the embodiment described above, same configurations, steps, and the like will be denoted by the same reference numerals and the like. As such, the following description will focus on differences between the present modification and the embodiment described above.

The present modification is configured such that after ST103 (start of operation of the light-emitting unit 8 of the blood detecting sensor 70) in the embodiment described above, in ST111, the infusion pump 10 detects negative pressure using the pressure sensor 77, and in ST112 after detecting the negative pressure, light quantity data detected by the blood detecting sensor 70 is requested.

Therefore, since a dislodgment of the catheter 5 can be judged based on light quantity data after the inside of the small diameter infusion tube 4b or the like is placed under negative pressure and a state is created where blood is suctioned from the blood vessel T, an accuracy of the judgment can be further improved.

In addition, since a frequency and timings of detection of blood by the blood detecting sensor 70 can be kept to the minimum necessary, power consumption of the blood detecting sensor 70 can be reduced and a battery-driven operating duration can be extended.

Figure 33:
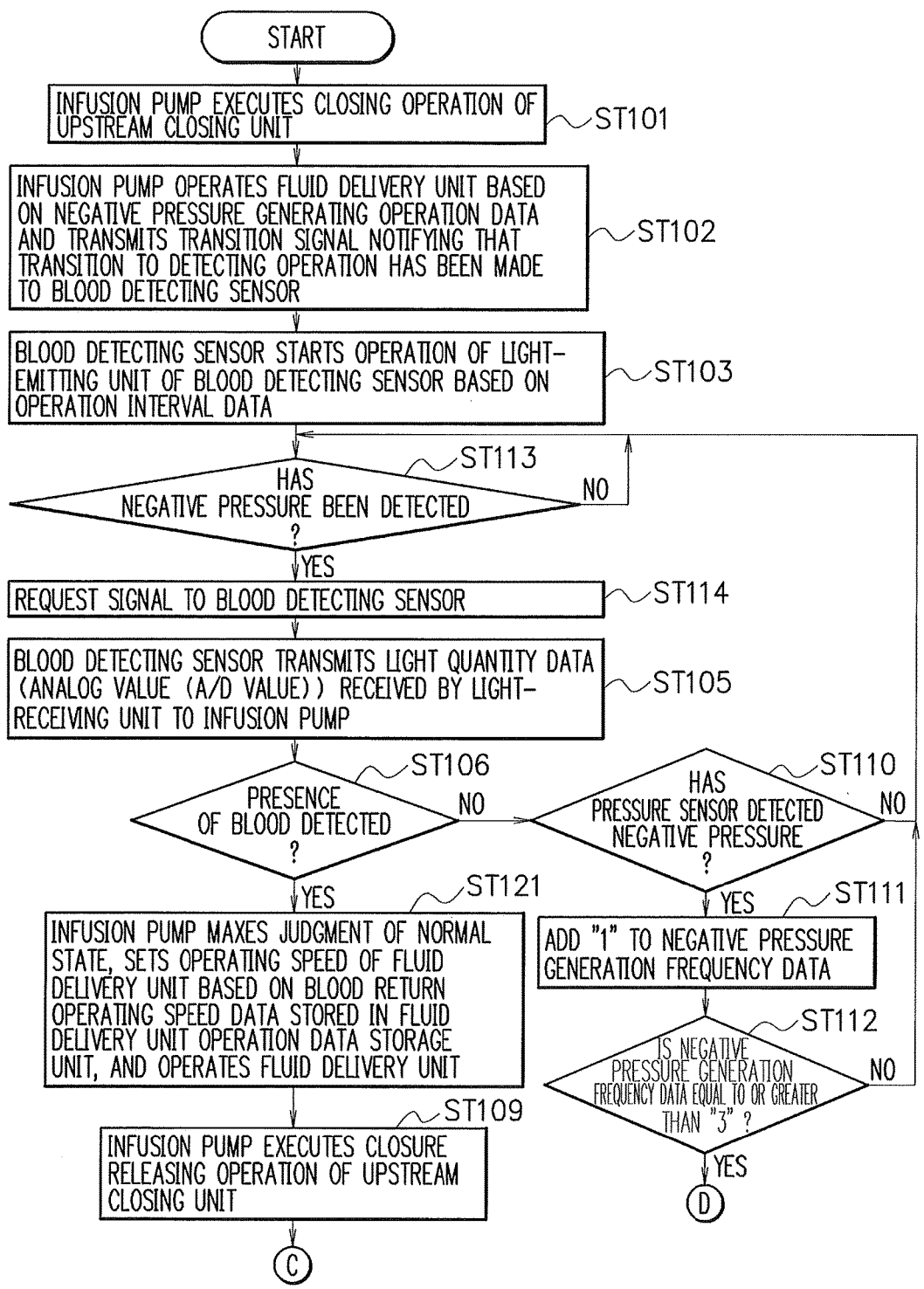
FIG. 33 is a schematic flow chart showing a second modification of the present embodiment.
Figure 34:
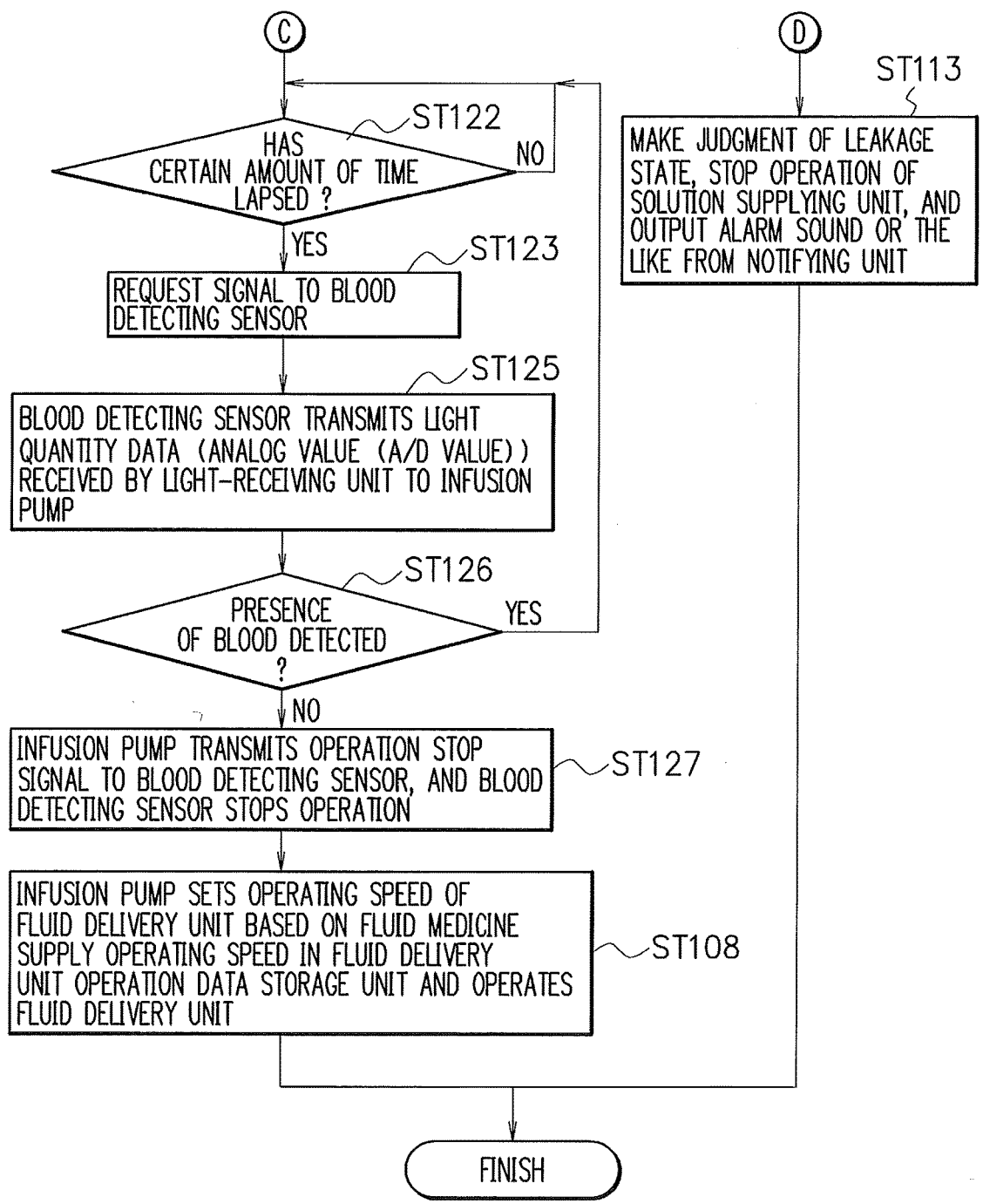
FIG. 34 is another schematic flow chart showing the second modification of the present embodiment.

FIGS. 33 and 34 are schematic flow charts showing a second modification of the present embodiment.

Since many components and steps of an operation example of the present modification are similar to those of the modification described above, same configurations and steps will be denoted by the same reference numerals and the like. As such, the following description will focus on differences between the present modification and the modification described above.

The present modification is configured such that ST121 is performed in place of ST107 of the first modification shown in FIG. 31 and described above, an execution sequence of ST108 and ST109 is changed, and respective steps of ST122 to ST127 are executed between ST109 and ST108.

In other words, first, ST121 is executed after ST106 (detection of presence of blood in the small diameter infusion tube 4*b* by the infusion pump 10).

In ST121, after judging that an arrangement state of the catheter 5 or the like is a normal state, the infusion pump 10 acquires blood return operating speed data stored in the fluid delivery unit operation data storage unit 81 shown in FIG. 7 and supplies a fluid medicine based on the data.

Although a configuration is realized in which blood inside the small diameter infusion tube 4*b* returns into the blood vessel T after negative pressure in the small diameter infusion tube 4*b* is released, this step is performed as a precaution in consideration of an unlikely case where blood remains inside the small diameter infusion tube 4*b*.

In particular, when a solution supplying speed of the fluid medicine W is low, a buildup of blood may conceivably result in the blood remaining as-is in the small diameter infusion tube 4*b*.

In consideration thereof, in the present embodiment, the fluid medicine W is supplied at an operating speed for returning blood after a light quantity detecting operation is performed by the blood detecting sensor 70 and before returning to normal supplying of the fluid medicine W.

Accordingly, the presence of residual blood in the small diameter infusion tube 4*b* can be completely eliminated and subsequent detection of a dislodgment of the catheter 5 or the like based on a light quantity detection by the blood detecting sensor 70 can be reliably performed.

FIG. 35 is a graph showing a relationship between pump flow rate and return (diameter 1.5 mm). FIG. 35 shows an operating speed for returning blood of the fluid delivery unit 20 described earlier in a case where the inner diameter of the small diameter infusion tube 4*b* is set to 1.5 mm.

As shown in FIG. 35, the operating speed for returning blood is preferably equal to or higher than 70 ml/h.

ST122 to ST127 in FIG. 34 are steps for confirming whether or not blood remains in the small diameter infusion tube 4*b* after performing an operation for returning blood.

Specifically, in ST122, the infusion pump 10 judges a lapse of a certain amount of time (for example, 1 second) and, subsequently, in ST123, the blood detecting sensor 70 is requested to transmit light quantity data.

Subsequently, in ST125, the received light quantity data is transmitted by the infusion pump 10.

The steps of ST123 and ST125 are similar to ST112 and ST105 shown in FIG. 31 of the first modification described earlier.

Next, the operation flow proceeds to ST126 to judge whether or not blood remains in the small diameter infusion tube 4*b* in a similar manner to ST106 shown in FIG. 31 of the first modification described earlier.

Subsequently, when the presence of blood is not detected in ST126, the operation flow proceeds to ST127 to execute a similar step to ST108 shown in FIG. 31 of the first modification described earlier for terminating the operation of the blood detecting sensor 70.

As shown, according to the present modification, the return of blood to the blood vessel T after a blood detecting operation performed by the blood detecting sensor 70 following negative pressure can be executed more reliably.

Moreover, the present invention is not limited to the embodiments described above.

REFERENCE SIGNS LISTS

1 infusion system
2 fluid medicine bag (fluid medicine containing unit)
3 instillation unit
4 infusion tube
4A upstream portion of infusion tube
4B downstream portion of infusion tube
4C connecting portion of infusion tube
5 catheter
10 infusion pump
20 fluid delivery unit
21 upstream closing unit
22 control unit
23 drive unit
24 notifying unit
25 output display unit
70, 170 blood detecting sensor
100, 100B extravasation detecting apparatus
173 condenser (charging unit)
180 first antenna unit
202 second antenna unit
W fluid medicine

The invention claimed is:

1. An extravasation detecting apparatus comprising:
   a fluid medicine containing unit which contains a fluid medicine and to which a catheter or an indwelling needle to be placed inside a blood vessel is connected by an infusion tube;
   a fluid delivery unit which supplies the fluid medicine by sequentially and repetitively pressing the infusion tube with a plurality of fingers;
   an upstream closing unit which is arranged at a portion of the infusion tube upstream the fluid delivery unit and which closes the infusion tube; and
   a blood detecting sensor which detects when blood is suctioned into the infusion tube from inside the blood vessel upon closing of an upstream portion of the infusion tube by the upstream closing unit when the fluid delivery unit is activated and negative pressure is generated in the infusion tube by a restoring force of the infusion tube, wherein
   when the blood detecting sensor detects that blood is being suctioned, a controller determines that a tip opening of the catheter or the indwelling needle is inside the blood vessel and an extravasation has not occurred, but when the blood detecting sensor detects that blood is not being suctioned, the controller determines that the tip opening is outside the blood vessel and an extravasation has occurred.

2. The extravasation detecting apparatus according to claim 1, wherein the blood detecting sensor is provided in a vicinity of the catheter or the indwelling needle in order to detect the blood that is suctioned into the infusion tube.

3. The extravasation detecting apparatus according to claim 2, wherein the blood detecting sensor comprises a light-emitting unit which irradiates light to the suctioned blood, a light-receiving unit which is arranged at a position facing the light-emitting unit across the infusion tube, and a main body unit which internally contains and holds the light-emitting unit and the light-receiving unit, wherein a light-blocking unit for blocking extraneous light is provided in the main body unit.

4. An infusion system comprising the extravasation detecting apparatus according to claim 2.

5. The extravasation detecting apparatus according to claim 1, wherein the blood detecting sensor is provided in a portion having a small inner diameter at a tip portion of the infusion tube.

6. The extravasation detecting apparatus according to claim 5, wherein the blood detecting sensor comprises a light-emitting unit which irradiates light to the suctioned blood, a light-receiving unit which is arranged at a position facing the light-emitting unit across the infusion tube, and a main body unit which internally contains and holds the light-emitting unit and the light-receiving unit, wherein
a light-blocking unit for blocking extraneous light is provided in the main body unit.

7. An infusion system comprising the extravasation detecting apparatus according to claim 5.

8. The extravasation detecting apparatus according to claim 1, wherein the blood detecting sensor comprises a light-emitting unit which irradiates light to the suctioned blood, a light-receiving unit which is arranged at a position facing the light-emitting unit across the infusion tube, and a main body unit which internally contains and holds the light-emitting unit and the light-receiving unit, wherein
a light-blocking unit for blocking extraneous light is provided in the main body unit.

9. The extravasation detecting apparatus according to claim 8, wherein the light-emitting unit performs pulsed emission at a frequency other than 50 Hz, 60 Hz, or a frequency that is a multiple thereof.

10. The extravasation detecting apparatus according to claim 9, wherein the blood detecting sensor includes a first antenna unit and a charging unit for feeding power to the light-emitting unit of the blood detecting sensor, the extravasation detecting apparatus further comprises a communication base unit that is separate from the blood detecting sensor, the communication base unit feeds power to the charging unit of the blood detecting sensor by electromagnetic induction with the first antenna unit of the blood detecting sensor, the blood detecting sensor transmits a signal, based on a detection result of a presence or absence of the blood in the infusion tube, from the first antenna unit of the blood detecting sensor to the base unit by wireless communication, and the communication base unit comprises a second antenna unit which notifies an infusion pump, which includes the fluid delivery unit, of the received signal based on the detection result of the presence or absence of the blood in the infusion tube to.

11. An infusion system comprising the extravasation detecting apparatus according to claim 9.

12. The extravasation detecting apparatus according to claim 8, wherein the blood detecting sensor includes a first antenna unit and a charging unit for feeding power to the light-emitting unit of the blood detecting sensor, the extravasation detecting apparatus further comprises a communication base unit that is separate from the blood detecting sensor, the communication base unit feeds power to the charging unit of the blood detecting sensor by electromagnetic induction with the first antenna unit of the blood detecting sensor, the blood detecting sensor transmits a signal, based on a detection result of a presence or absence of the blood in the infusion tube, from the first antenna unit of the blood detecting sensor to the base unit by wireless communication, and the communication base unit comprises a second antenna unit which notifies an infusion pump, which includes the fluid delivery unit, of the received signal based on the detection result of the presence or absence of the blood in the infusion tube to.

13. An infusion system comprising the extravasation detecting apparatus according to claim 12.

14. An infusion system comprising the extravasation detecting apparatus according to claim 8.

15. An infusion system comprising the extravasation detecting apparatus according to claim 1.

16. An extravasation detecting apparatus comprising:
a fluid medicine containing unit which contains a fluid medicine, the fluid medicine containing unit being connected to an infusion tube having a distal end connected to either a catheter or an indwelling needle to be positioned inside a blood vessel;
a fluid delivery unit which supplies the fluid medicine in the fluid medicine containing unit to the catheter or the indwelling needle by sequentially and repetitively pressing the infusion tube with a plurality of fingers;
an upstream closing unit arranged at a portion of the infusion tube upstream of the fluid delivery unit to close the infusion tube;
a blood detecting sensor which detects when blood is suctioned into the infusion tube from inside the blood vessel when an upstream portion of the infusion tube is closed by the upstream closing unit and when the fluid delivery unit is activated and generates negative pressure in the infusion tube by a restoring force of the infusion tube;
the blood detecting sensor being provided in a vicinity of the catheter or the indwelling needle to detect the blood that is suctioned into the infusion tube from inside the blood vessel;
the blood detecting sensor comprising a light-emitting unit and a light-receiving unit both positioned outside the infusion tube so that a portion of the infusion tube is positioned between the light-emitting unit and the light-receiving unit, the light-emitting unit irradiating light at the portion of the infusion tube positioned between the light-emitting unit and the light-receiving unit so that blood passing through the infusion tube blocks the light directed at the portion of the infusion tube;
the light-receiving unit detecting the blood passing through the infusion tube by detecting a variable component of received light quantity that is being blocked by blood passing through the infusion tube; and
the passage of the blood through the infusion tube being detected based on the variable component of received light quantity detected by the light-receiving unit.

17. A method comprising:
introducing a tip of a device into a blood vessel, the device being connected to an infusion tube which in turn is connected to a fluid medicine containing unit so that the device is in fluid communication with the fluid medicine containing unit, the device being either a catheter or an indwelling needle;
generating negative pressure in the infusion tube at a position upstream of the device;
detecting whether blood has been drawn into the infusion tube from inside the blood vessel; and
determining that the tip of the device is inside the blood vessel and an extravasation has not occurred when blood is detected to have been drawn into the infusion tube from inside the blood vessel, and determining that the tip of the device is no longer inside the blood vessel and an extravasation has occurred when blood is detected to not have been drawn into the infusion tube.

18. The method according to claim 17, wherein the generating of the negative pressure in the infusion tube at the position upstream of the device includes closing off the infusion tube at the position upstream of the device while a pressing force is applied to a portion of the infusion tube, and then releasing the pressing force while the infusion tube remains closed off at the position upstream of the device, the portion of the tube at which the pressing force is applied being located between the device and the position upstream of the device.

19. The method according to claim 17, further comprising delivering the fluid medicine in the fluid medicine containing unit to the tip of the device by sequentially and repetitively pressing the infusion tube with a plurality of fingers, the delivery of the fluid medicine in the fluid medicine containing unit to the tip of the device occurring before generating the negative pressure in the infusion tube.

20. The method according to claim 17, further comprising irradiating light at a portion of the infusion tube, the light being emitted by a light-emitting unit and being received by a light-receiving unit, the infusion tube being positioned between the light-emitting unit and the light-receiving unit, the method further comprising detecting blood passing through the infusion tube by detecting a variable component of received light quantity that is being blocked by blood passing through the infusion tube.

\* \* \* \* \*